(12) United States Patent
Tal et al.

(10) Patent No.: US 7,967,834 B2
(45) Date of Patent: Jun. 28, 2011

(54) VASCULAR TREATMENT DEVICE

(75) Inventors: Michael G. Tal, Woodbridge, CT (US);
John P. Marano, Jr., Madison, CT (US);
Stanley O. Thompson, New Boston, NH (US); Chris Labak, Milford, NH (US)

(73) Assignee: Vascular Insights LLC, Madison, CT (US)

( * ) Notice: Subject to any disclaimer, the term of this patent is extended or adjusted under 35 U.S.C. 154(b) by 202 days.

(21) Appl. No.: 12/438,314

(22) PCT Filed: Sep. 13, 2007

(86) PCT No.: PCT/US2007/078367
§ 371 (c)(1),
(2), (4) Date: Feb. 20, 2009

(87) PCT Pub. No.: WO2008/033983
PCT Pub. Date: Mar. 20, 2008

(65) Prior Publication Data
US 2009/0270889 A1    Oct. 29, 2009

Related U.S. Application Data

(60) Provisional application No. 60/825,529, filed on Sep. 13, 2006, provisional application No. 60/916,110, filed on May 4, 2007.

(51) Int. Cl.
*A61B 17/3207* (2006.01)
(52) U.S. Cl. ........................ 606/159; 606/180
(58) Field of Classification Search .................... 606/79, 606/80, 159, 167–180, 81, 127, 128; 604/22, 604/110, 111, 103.05, 192; 200/43.09, 51 R, 200/51.09, 51.1
See application file for complete search history.

(56) References Cited

U.S. PATENT DOCUMENTS

| | | | |
|---|---|---|---|
| 4,867,156 A * | 9/1989 | Stack et al. | 606/159 |
| 4,906,236 A * | 3/1990 | Alberts et al. | 604/198 |
| 5,047,013 A | 9/1991 | Rossdeutscher | |
| 5,087,244 A | 2/1992 | Wolinsky et al. | |
| 5,087,265 A * | 2/1992 | Summers | 606/159 |
| 5,269,794 A * | 12/1993 | Rexroth | 606/180 |

(Continued)

FOREIGN PATENT DOCUMENTS

CA         2405273         10/2001

(Continued)

OTHER PUBLICATIONS

International Search Report for PCT/US2007/078367.

(Continued)

*Primary Examiner* — Kathleen Sonnett
(74) *Attorney, Agent, or Firm* — Scott E. Kamholz; Foley Hoag LLP

(57) ABSTRACT

A vascular treatment device may include (1) a handle having a motor, a trigger, and a male coupling, and (2) a cartridge, engageable to the handle, having a female coupling, a wire, and a sheath fixed to the cartridge. When the female coupling is not engaged to the male coupling, the sheath may cover the distal end of the wire, allowing safe advancement of the device into the patient's vasculature, and when the female coupling is engaged by the male coupling, the distal end of the wire may be exposed from the sheath and used.

50 Claims, 31 Drawing Sheets

U.S. PATENT DOCUMENTS

| | | | |
|---|---|---|---|
| 5,415,636 A | | 5/1995 | Forman |
| 5,611,357 A | | 3/1997 | Suval |
| 5,628,730 A | | 5/1997 | Shapland et al. |
| 5,632,755 A | * | 5/1997 | Nordgren et al. ............. 606/159 |
| 5,675,228 A | * | 10/1997 | O'Bryan ....................... 318/453 |
| 5,709,657 A | | 1/1998 | Zimmon |
| 5,716,366 A | | 2/1998 | Yates |
| 5,766,191 A | | 6/1998 | Trerotola |
| 5,836,905 A | | 11/1998 | Lemelson et al. |
| 5,902,266 A | | 5/1999 | Leone et al. |
| 5,911,700 A | | 6/1999 | Mozsary et al. |
| 5,976,164 A | * | 11/1999 | Bencini et al. ................ 606/170 |
| 6,048,332 A | | 4/2000 | Duffy et al. |
| 6,090,118 A | | 7/2000 | McGuckin, Jr. |
| 6,159,196 A | | 12/2000 | Ruiz |
| 6,165,187 A | * | 12/2000 | Reger ............................ 606/159 |
| 6,231,518 B1 | | 5/2001 | Grabek et al. |
| 6,273,882 B1 | * | 8/2001 | Whittier et al. .................... 606/1 |
| D450,843 S | | 11/2001 | McGuckin, Jr. et al. |
| 6,369,039 B1 | | 4/2002 | Palasis et al. |
| 6,482,215 B1 | * | 11/2002 | Shiber ............................ 606/159 |
| 6,484,727 B1 | | 11/2002 | Vaska et al. |
| 6,544,221 B1 | | 4/2003 | Kokish et al. |
| 6,602,264 B1 | | 8/2003 | McGuckin, Jr. |
| 6,673,025 B1 | | 1/2004 | Richardson et al. |
| 6,679,886 B2 | * | 1/2004 | Weikel et al. .................... 606/79 |
| 6,824,550 B1 | * | 11/2004 | Noriega et al. ............... 606/159 |
| 6,824,551 B2 | | 11/2004 | Trerotola |
| 6,852,118 B2 | | 2/2005 | Shturman et al. |
| 7,025,774 B2 | | 4/2006 | Freeman et al. |
| 7,108,704 B2 | | 9/2006 | Trerotola |
| 2002/0010418 A1 | | 1/2002 | Lary et al. |
| 2002/0077594 A1 | | 6/2002 | Chien et al. |
| 2002/0188276 A1 | | 12/2002 | Evans et al. |
| 2003/0045860 A1 | | 3/2003 | Leu |
| 2003/0120256 A1 | | 6/2003 | Lary et al. |
| 2004/0092967 A1 | | 5/2004 | Sancoff et al. |
| 2005/0055040 A1 | | 3/2005 | Tal |

FOREIGN PATENT DOCUMENTS

| | | |
|---|---|---|
| CN | 2148536 Y | 12/1993 |
| DE | 10059742 | 6/2002 |
| EP | 0501081 | 9/1992 |
| FR | 2651682 | 3/1991 |

OTHER PUBLICATIONS

Written Opinion for PCT/US2007/078367.
Williams et al., "Sclerosant Treatment of Varicose Veins and Deep Vein Thrombosis," *Archives of Surgery*, vol. 119, No. 11, Nov. 1984.

* cited by examiner

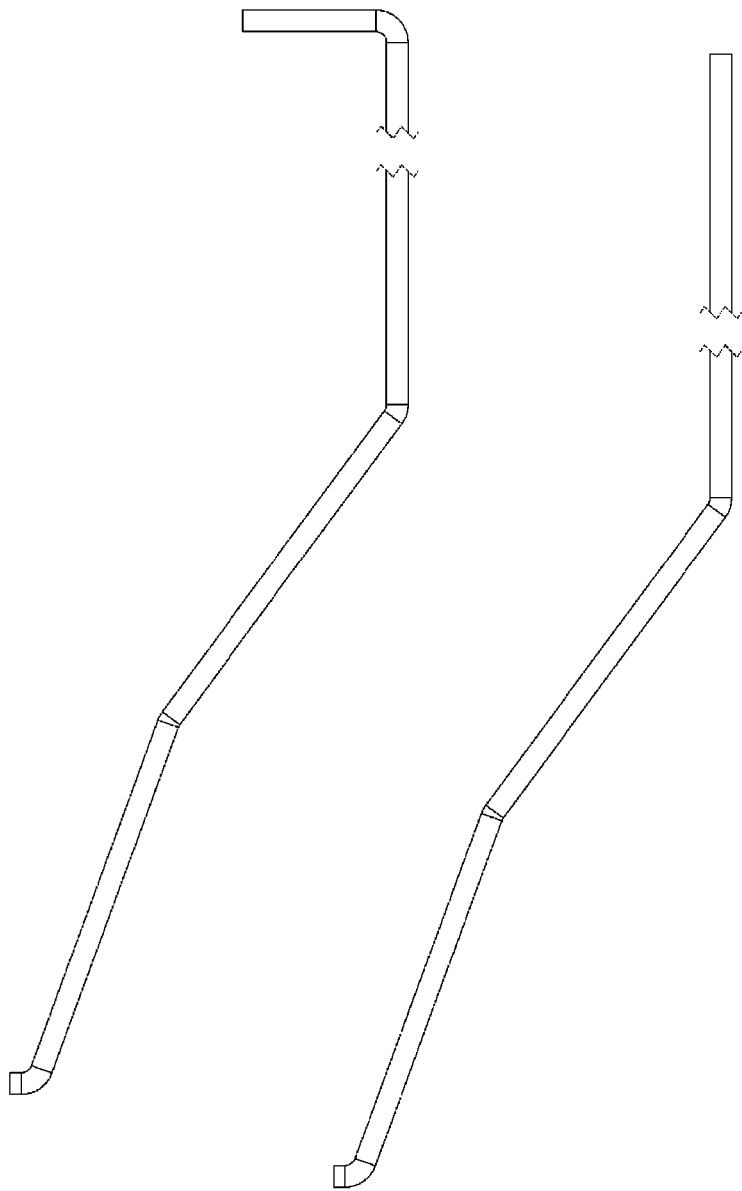
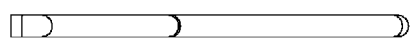
FIG. 14

FIG. 14A

FIG. 15A

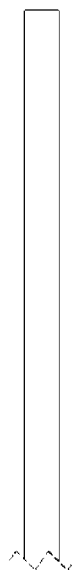
FIG. 16A

FIG. 17A

FIG. 18A

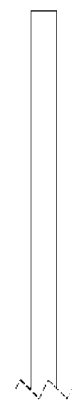
FIG. 19A

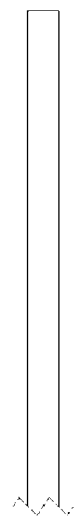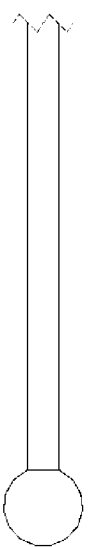
FIG. 20A

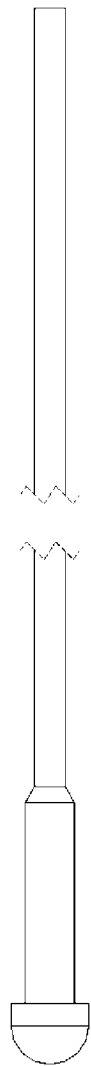
FIG. 21A

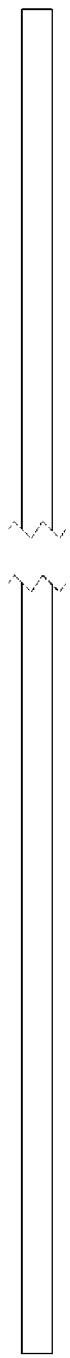
FIG. 22A

VASCULAR TREATMENT DEVICE

CROSS-REFERENCE TO RELATED APPLICATIONS

This application is the national stage of International Application No. PCT/US2007/078367, filed on Sep 13, 2007, which claims the benefit of U.S. Provisional application Nos. 60/825,529, filed Sep. 13, 2006, and 60/916,110, filed May 4, 2007, both of which are hereby incorporated herein by reference.

SUMMARY

A vascular treatment device may include (1) a handle having a motor, a trigger, and a male coupling, and (2) a cartridge, engageable to the handle, having a female coupling, a wire, and a sheath fixed to the cartridge. When the female coupling is not engaged to the male coupling, the sheath may cover the distal end of the wire, allowing safe advancement of the device into the patient's vasculature, and when the female coupling is engaged by the male coupling, the distal end of the wire may be exposed from the sheath and used.

BRIEF DESCRIPTION OF THE DRAWINGS

FIGS. 14-14A, 15-15A, 16-16A, 17-17A, 18-18A, 19-19A, 20-20A, 21-21A, 22-22A, 23, and 24 depict various embodiments of wire distal ends.

DETAILED DESCRIPTION

A vascular treatment device may be used for ablating blood vessels, such as varicose veins, and for treating thrombosis by macerating a clot and injecting a thrombolytic drug, among other uses. A vascular treatment device may include a rotatable wire, so sized and shaped for ablating blood vessels, coupled to a cartridge that is engageable to a handle. The wire may thus be indirectly engaged with a motor in the handle such that the wire rotates when the motor is turned on. When the device is used for treating a varicose vein, the rotating wire may perturb the vessel to cause vasospasm, a condition in which blood vessels spasm, and may cause damage to the vessel wall to promote sclerosis. During a thrombectomy procedure, the wire may macerate a clot without causing damage to the vessel wall.

Figure 1:
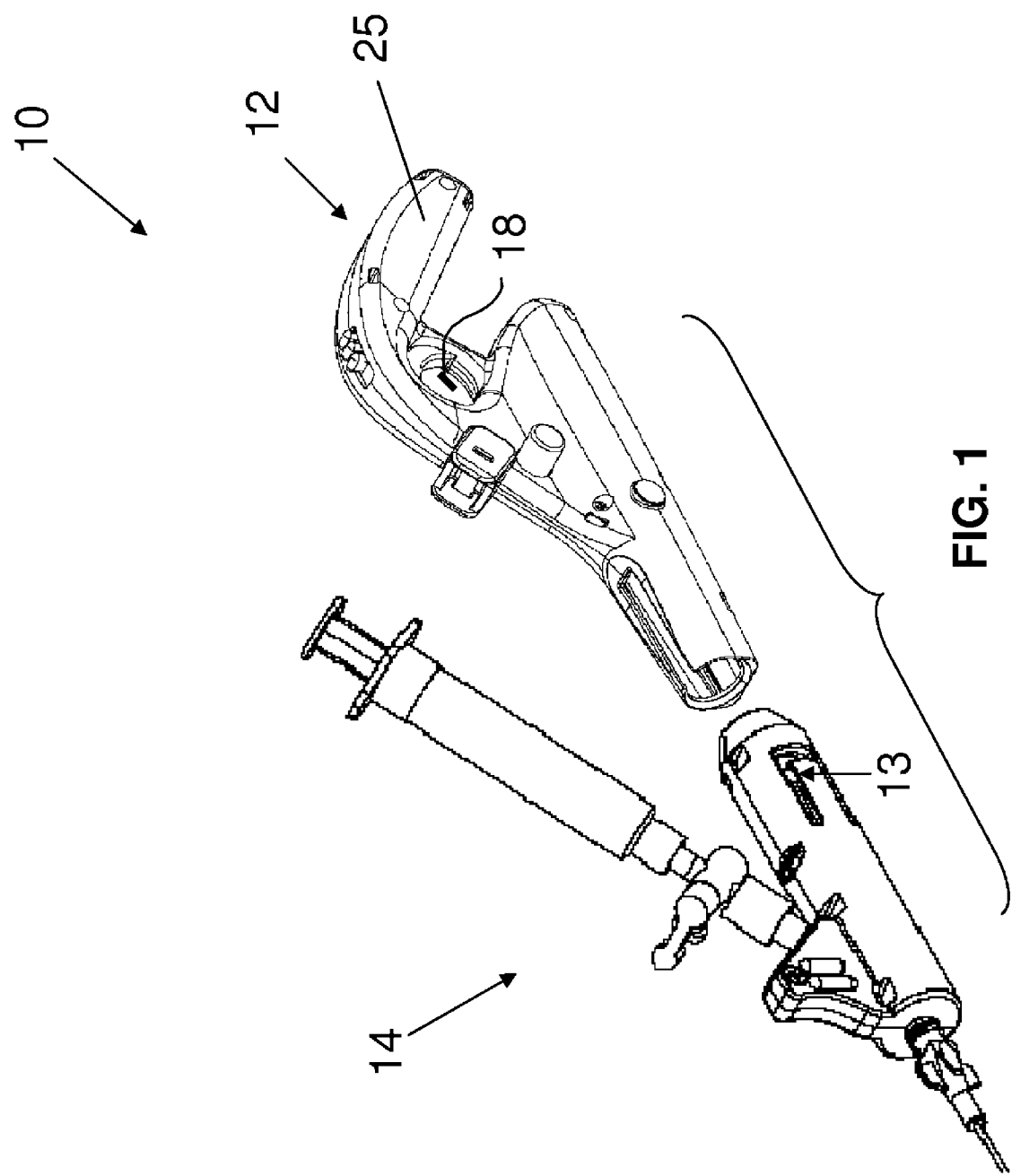
FIG. 1 shows an embodiment of an assembly of a vascular treatment device.
Figure 2:
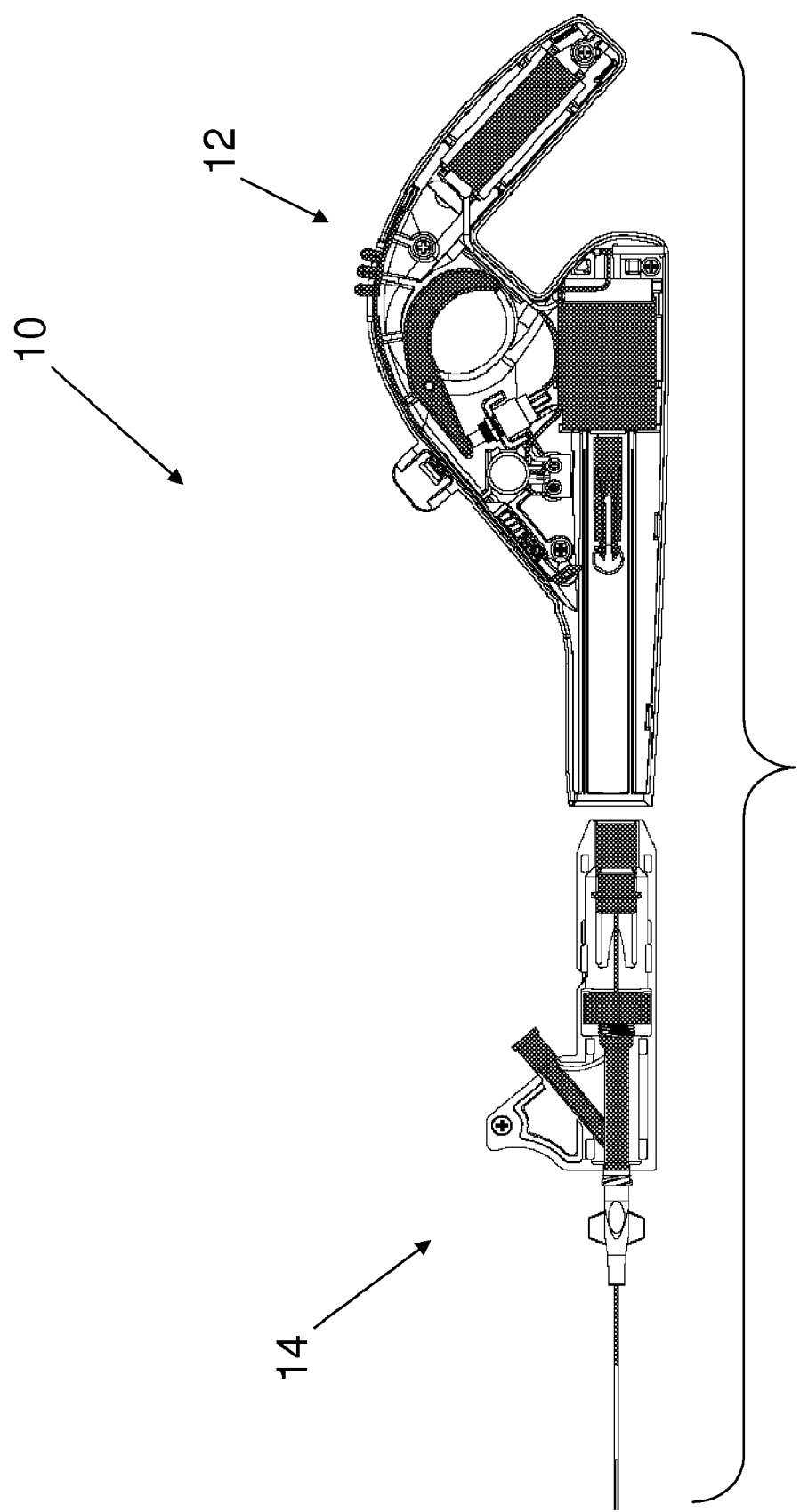
FIG. 2 illustrates a longitudinal cross-sectional view of the embodiment illustrated in FIG. 1.

FIG. 1 shows an embodiment of an assembly of a vascular treatment device 10 having a handle 12 and a cartridge 14. The cartridge 14 may be so sized and shaped to engage to the handle 12 by fitting one component to another as shown. An embodiment of the handle 12 is shown in greater detail in FIG. 3. The handle may define a receptacle 29 in which the male coupling 30 is positioned to receive the female coupling 40 of the cartridge 14 when the cartridge 14 and the handle 12 engage. The handle 12 may include a motor 22, a trigger 26, and a male coupling 30. The male coupling 30 may be connected to the motor 22 in such a way that the motor rotably drives the male coupling upon activation. A potentiometer 24 may be electrically coupled to the motor 22 to control a speed of the motor. The trigger 26 may be mounted on the handle and transitionable between a first state, which does not couple the motor to a power source electrically, and a second state, which couples the motor to a power source.

The handle 12 may also include a power source 20 and a microswitch 28 connected to the motor 22 by a wire 32. The microswitch 28 may be interposed in an electrical circuit connecting the trigger 26 and the motor 22. The microswitch may be biased to an open position such that the circuit between the trigger and the motor is open. When the cartridge 14 is engaged in the handle 12, the cartridge may press against the microswitch, causing it to transition to a closed state, thereby completing the electrical circuit connecting the trigger 26 and motor 22. For example, the microswitch may include two contacts with a conductor that is attached to one contact and disconnected from the second contact when the microswitch is in an open state. In one embodiment, the conductor may include a strip of metal that hangs in the channel into which the cartridge is slid during engagement with the handle. As the cartridge is engaged in the handle, it pushes the metal strip out of the channel and into connection with the second contact of the microswitch. One advantage gained from such configuration may be that a user will not be able to activate the device inadvertently by pressing on the trigger before he/she is ready to use the device, i.e., before the cartridge 14 is fully engaged to the handle 12.

Figure 3:
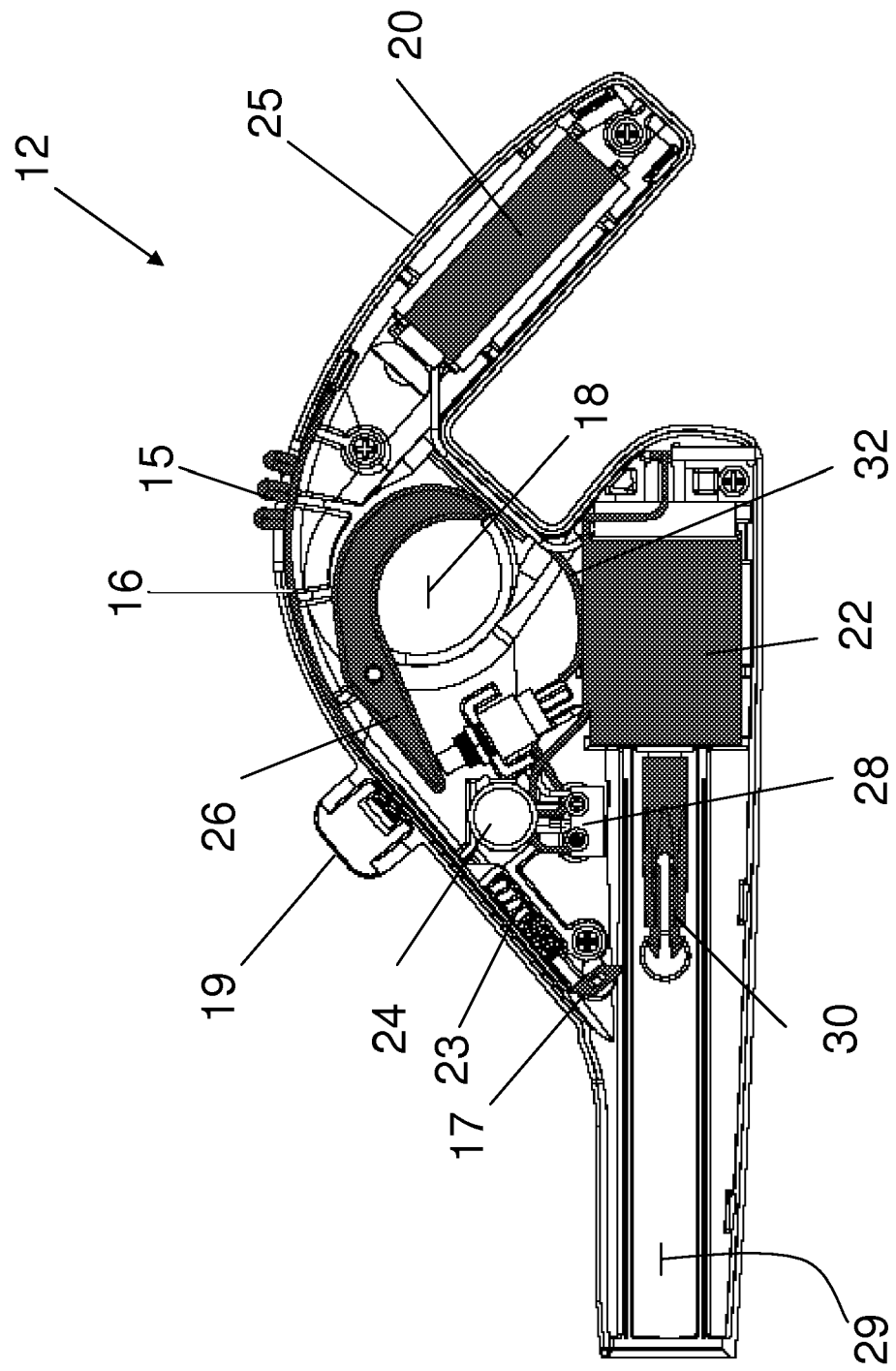
FIG. 3 shows a longitudinal cross-sectional view of a handle.

The handle may 12 also include a switch 16 as shown in FIG. 3. The switch 16 allows the cartridge 14 to be received by, and secured in, the handle 12. The switch may include a grip 15 to permit a user to operate the switch with a finger. The switch may also include a gate 17 that alternately obstructs or locks the cartridge, depending on the gate's position. For example, a user may put a thumb on the grip 15 and push the switch 16 away from the handle grip 25 to transition the switch 16 from a first position, in which gate 17 is positioned in the channel and so prevents engagement of the cartridge 12 and the handle 14, to a second position in which gate 17 is moved out of the channel and thereby permits engagement of the cartridge and the handle. Upon release of the biased switch 16, the gate 17 may fit into a complementary detent in the cartridge and thereby help keep the cartridge engaged with the handle.

The gate 17 may be biased to the first position by a spring 23 contacting the handle. As the user pushes the switch 16 away from the handle grip 25, the switch 16 will push on the spring, thereby creating a restoring force to urge the switch to its original position once the user releases the switch.

As noted above, the gate 17 may be further transitionable to a third position which prevents disengagement of the cartridge 14 from the handle 12. For example, the gate 17 may be forced into the detent 35 (shown in FIG. 4), defined by the cartridge 14, when the biased switch 16 returns to its original position from the second position to lock the cartridge to the handle.

One or more portions of the handle 12 may define a trigger ring 18 in which the trigger is at least partly disposed and about which the handle is so arranged as to be balanced when supported from only one or more portions of the handle that define the trigger ring. In this manner, a user may balance the handle simply by supporting it with a single finger, such as an index finger, against a portion of the handle that defines the trigger ring 18. As motor 22 may well be the heaviest component in the handle, it can be positioned below the trigger 26 as shown in FIG. 3 to reduce the bending moment applied by the motor 22 on a finger supporting the handle by the trigger ring, thereby reducing fatigue experienced by the user.

The handle 12 may be formed by joining two outer casing pieces together.

Figure 4:
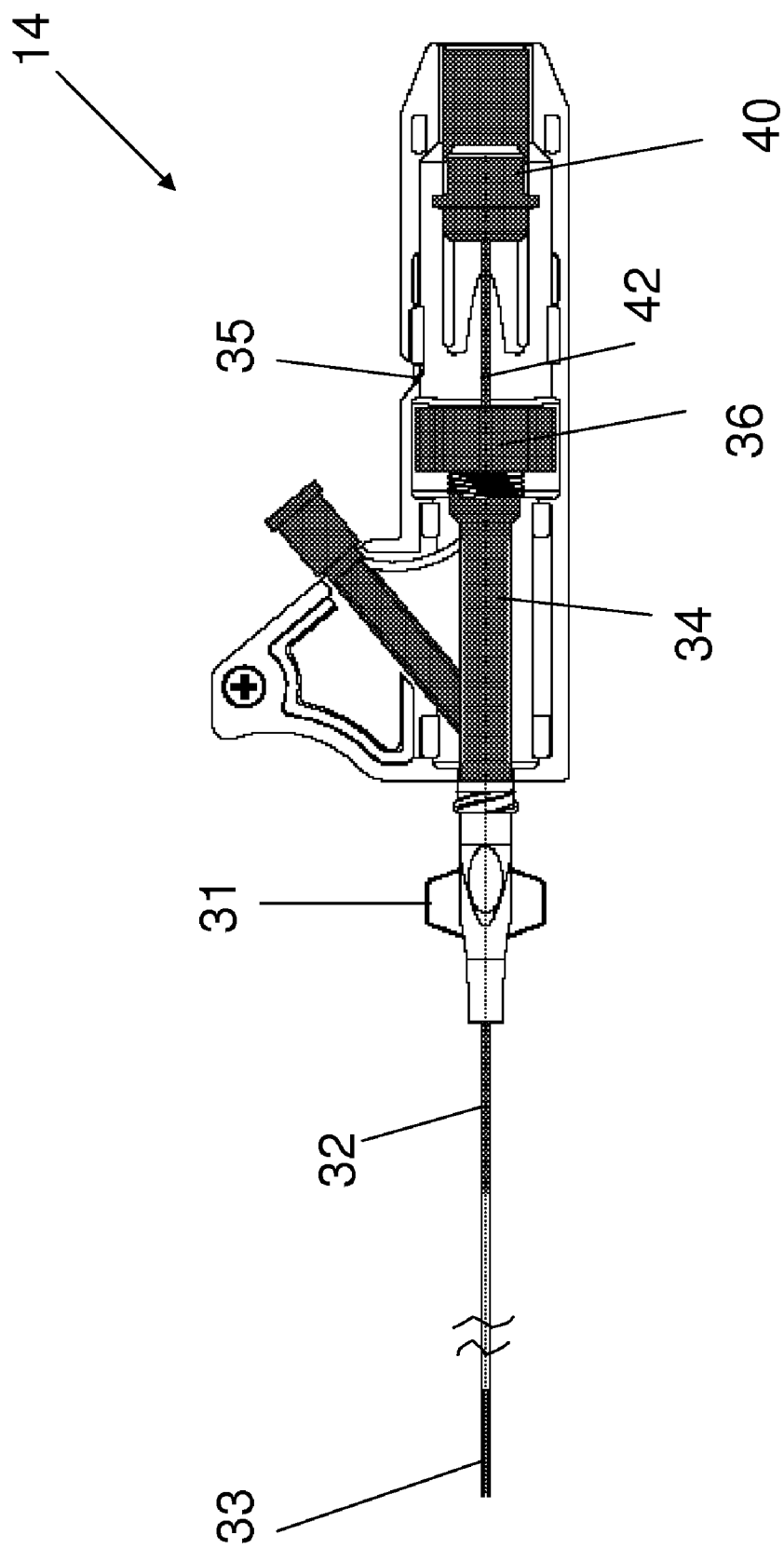
FIG. 4 illustrates a longitudinal cross-sectional view of a cartridge.

An embodiment of the cartridge 14 shown in FIG. 1 is illustrated in greater detail in FIG. 4. The cartridge 14 may include a female coupling 40, a wire 33 (shown as a broken line), and a sheath 32 fixed to and extending from the cartridge 14. The wire may be fixed to the female coupling 40; for example, the wire's proximal tip may be bent approximately 90 degrees to fit through a channel that is sized and shaped to receive the bent end of the wire. A setscrew may be received in the female coupling 40 and/or an appropriate adhesive may be used to secure the wire and prevent it from rotating with respect to the female coupling.

The sheath 32 may define a lumen through which the wire 33 runs. The sheath 32 may have a wide range of inner and outer diameters. In some embodiments, the sheath may have an inner diameter in the range of from 0.022 inches to 0.048 inches. In some embodiments, the sheath 32 may have an outer diameter in the range of from 0.025 inches to 0.051 inches. The outer diameter of the sheath may also be in the range that is consistent with the standard needles having corresponding inner diameters. For example, the sheath may be so sized and shaped to be insertable in a standard needle or vascular sheath having an inner diameter in the range of from 0.0035 inches to 0.1060 inches, or from 0.0160 inches to 0.0420 inches, or from 0.0420 inches to 0.0630 inches, or from 0.0115 inches to 0.0630 inches. The maximum outer diameter of the sheath may be less than 0.035 inches to allow the sheath to be inserted through a intravenous needle or catheter having an inner diameter of less than 0.0039 inches to allow a wider range of practitioners to perform the procedure. Needles, catheters or vascular sheaths with an outer diameter greater than 0.079 inches (6 French, Fr) or 0.092 inches (7 Fr) typically require insertion to be performed by a vascular surgeon or interventional radiologist.

The sheath 32 may also include external markings at regular intervals which may guide the user to monitor the insertion or removal speed of the device 10.

Figure 5:
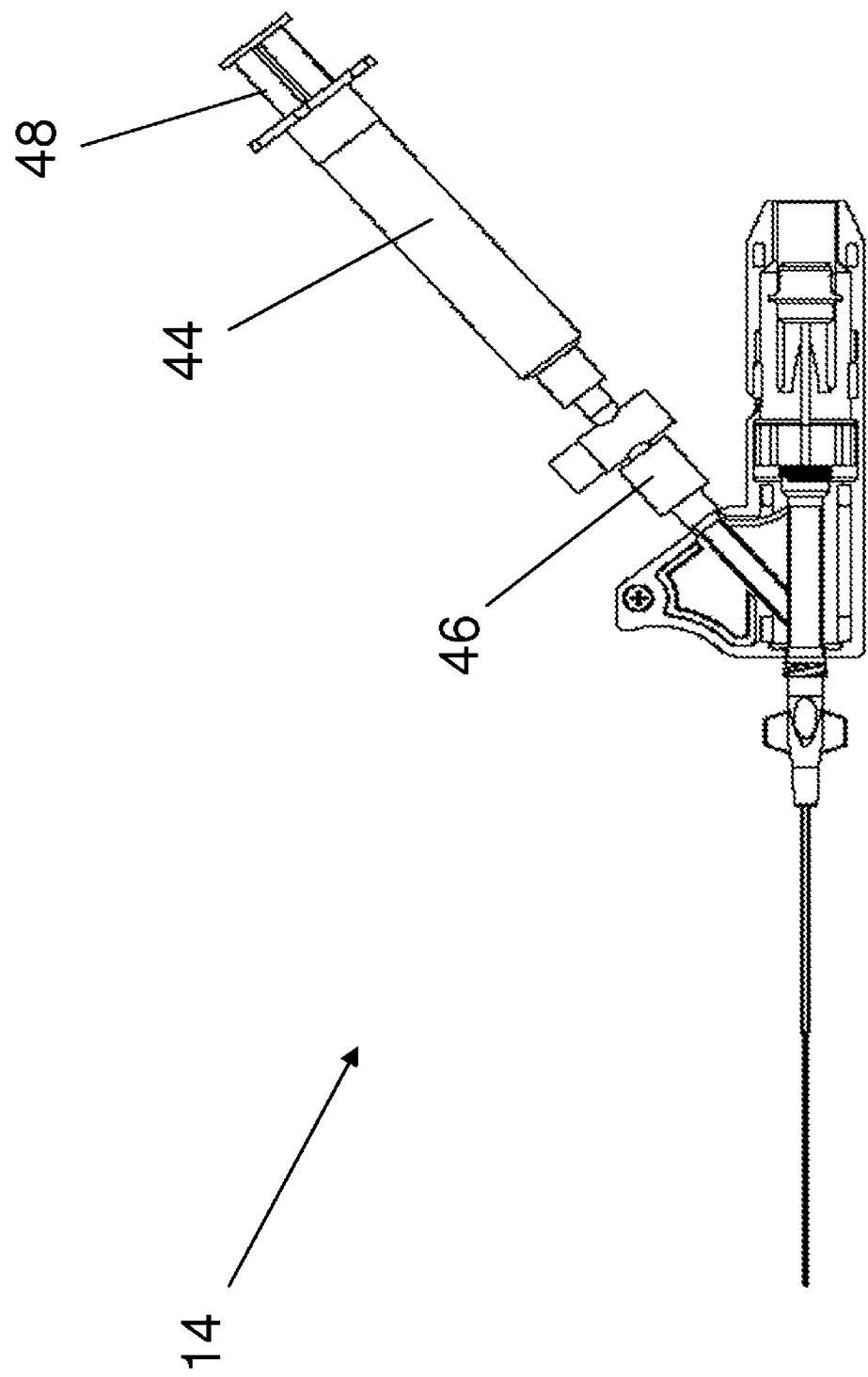
FIG. 5 shows the cartridge illustrated in FIG. 4 with a syringe and a stopcock attached.

One exemplary embodiment depicting a reservoir connectable to the cartridge may include a syringe 44, a stopcock 46, and a plunger 48 as shown in FIG. 5. The syringe 44 may be in fluid communication with the bore of the sheath 32 for releasing a substance at the wire distal end, such as a sclerosant (examples of which include polidocanol, sodium tetradecyl sulfate, and hypertonic saline), or thrombolytic drug (examples of which include alteplase (Activase), anistreplase (Eminase), streptokinase (Streptase, Kabikinase), urokinase (Abbokinase), and tissue plasminogen activator (TPA). In this manner, physical perturbation by the wire may be synergistically combined with drug treatment to improve device efficacy.

The handle 12 may include a support 19 (shown in FIG. 3) so positioned as to receive the syringe 44. The support 19 may be so sized and shaped to be compatible with the standard syringes and may prevent the syringe from falling out during injection, especially if the material being injected has high volume and/or viscosity and requires significant user thumb pressure upon the syringe. When the cartridge 14 with an attached syringe 44 is engaged to the handle, the syringe 44 may snap onto the support 19. As shown in FIG. 1, the support may be formed from two brackets which cradle the syringe. An alternative embodiment shown in FIGS. 6 and 7 includes a support formed from a single hook that wraps partially around the syringe. These embodiments allow use of the device with the right as well as left hand, depending on the user's preference and/or the patient's position on the treatment table.

The handle 12 and the syringe 44 may be so sized, shaped, and positioned as to permit a user to actuate the trigger 26 with the index finger of a hand and simultaneously depress a plunger 48 into the syringe with the thumb of the same hand, allowing a treatment drug to be deployed from the syringe through the sheath while the wire 33 is rotating. For example, a user may hold the handle by positioning the handle grip 25 in the center of the palm and wrapping third, fourth, and fifth finger around the handle grip and putting an index finger through the trigger ring 18 and if needed, placing a thumb to depress the plunger to release treatment drug into the syringe. The handle may be so designed to allow both right- and left-handed users to operate.

The stopcock 46 shown in FIG. 5 may allow reloading of fluid and also changing the fluid concentration of composition as well as mixing of the sclerosant fluid with gas. For example, air can be mixed for generating foam as well as agitating existing sclerosant/gas mixture and also recreating the foam, because the foam has a limited duration (typically a minute or less) before the fluid and gas start to separate. The stopcock 46 may allow the fluid composition mixture to be agitated without disconnecting the syringe from the cartridge or without stopping the procedure.

A standard Y hemostasis connector 34 as shown in FIG. 4, or other Y hemostasis connector, may be used to aid in fluid communication between the syringe 44 and the lumen defined by the sheath 32. A Y-hemostasis connector 34 may be connected to the female luer hub 31 and to the tubing nut 36 to prevent the fluid from leaking into the region containing the motor 22. An O-ring may be used to prevent leaks around the wire shaft. Wire tubing 42 may be so sized and shaped to receive the wire 33 and attached to the female coupling 40. Combining the above mentioned components may allow the motor to rotate the wire without increasing the torque beyond the appropriate working range. The motor may spin in the range of from 500 to 3000 rpm-4000 rpm for varicose vein destruction and thrombectomy procedures. The handle may also include a built-in RPM display for user to read the speed or may include an electrical port through which the speed may measured by an external monitor.

The male coupling 30 on the handle 12 may be biased toward an expanded state and transitionable from the expanded state to a contracted state. The female coupling 40 may be so sized and shaped as to transition the male coupling 30 from the expanded state to the contracted state during engagement of the handle 12 and the cartridge 14. As the male coupling 30 and the female coupling 40 fully engage each other, the male coupling displaces the female coupling detents 13 to allow the female coupling to slide within the cartridge.

Attaching the female coupling 40 to the male coupling 30 thereby causes the sheath 32 to slide back relative to the wire. This occurs because the sheath is fixed to the cartridge, while the wire is fixed to the female coupling. As the cartridge is fully seated in the handle, the female coupling is pushed forward in the cartridge. So when the female coupling 40 is not engaged by the male coupling 30, the sheath 32 may cover the distal end of the wire 33, allowing it to be safely advanced in the patient's vasculature; and when the female coupling 40 is engaged by the male coupling 30, the sheath may reveal the distal end of the wire. Consequently, when the female and male couplings are engaged (1) the distal tip of the wire is revealed, and (2) the wire is operably coupled to the motor 22 through the female and male couplings, to allow the motor to rotate the wire 33. As noted above, the cartridge may also trip a lever arm coupled to the microswitch 28 to complete a circuit between the trigger 26 and the motor 22. The male coupling 30 may be so sized and shaped as to return to the expanded state once the cartridge 14 and the handle 12 are fully engaged as described earlier.

The female coupling may be disengaged from the male coupling to re-cover the distal tip of the wire when the wire is to be removed for the site of use, or if a treatment is interrupted. Disengaging the female coupling from the male coupling slides the wire 33 with respect to the sheath 32 (attached to the cartridge fixed to the handle); as a result the tip of the wire is no longer exposed, allowing it to be safely removed. This mechanism may protect the tip of the wire 33 prior to use and also protect the blood vessels and other body tissues during removal or repositioning of the device.

The male coupling 30 may have at least two prongs separated by slitted portions to facilitate the transition from the expanded state to the contracted state. The male coupling may be made with polycarbonate, plastic, or other materials which allow transitioning between an expanded state to a contracted state.

In some embodiments, the vascular treatment device 10 may be of a single piece construct having a handle and a cartridge. The cartridge may be assembled to the handle during manufacturing and be able to transition within the handle between a first position, where the male and female couplings are not engaged, and a second position, where the male and female couplings are engaged. An embodiment of such device may allow the cartridge to slide back and forth within a predetermined range, such as the first and the second position, in the groove defined by the handle, but the cartridge may not disengage itself from the handle. A sheath may be fixed and extend from the cartridge and define a lumen through which the wire runs. The cartridge may also include a syringe to be received by a support mounted on the handle.

In this embodiment, the handle may include a motor, a motor coupling, a trigger, and a power source. The wire having a main shaft, a distal end, and a proximal end which is fixed to the motor coupling may be attached to the motor coupling. The motor coupling may be rotably driven by the motor. The trigger may be mounted on the handle and be transitionable between a first state, which does not couple the motor to a power source electrically, and a second state, which couples the motor to a power source. The handle may also include a microswitch to permit trigger and the motor to be electrically coupled to one another.

At the first position, the cartridge may cover the distal tip of the wire. At the second position, the cartridge (1) exposes the distal tip of the wire from the sheath, and (2) completes a circuit between the trigger and the motor by tripping a lever arm coupled to the microswitch. Therefore, the single piece construct vascular treatment device may allow a user to obtain similar functionality as the device explained earlier and shown in FIG. 1.

Figure 6:
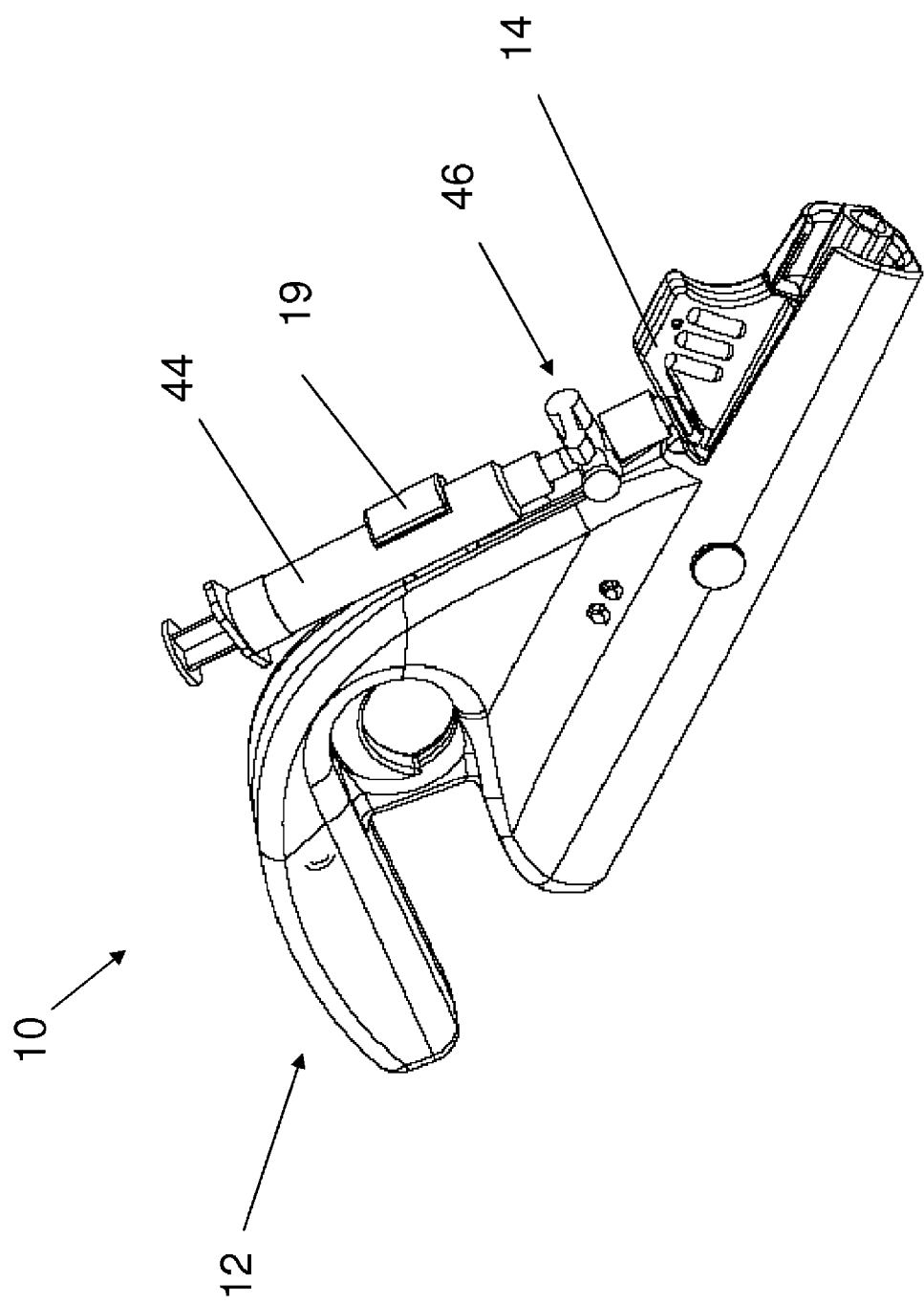
FIG. 6 shows a perspective view of an embodiment of a vascular treatment device having a single syringe support.
Figure 7:
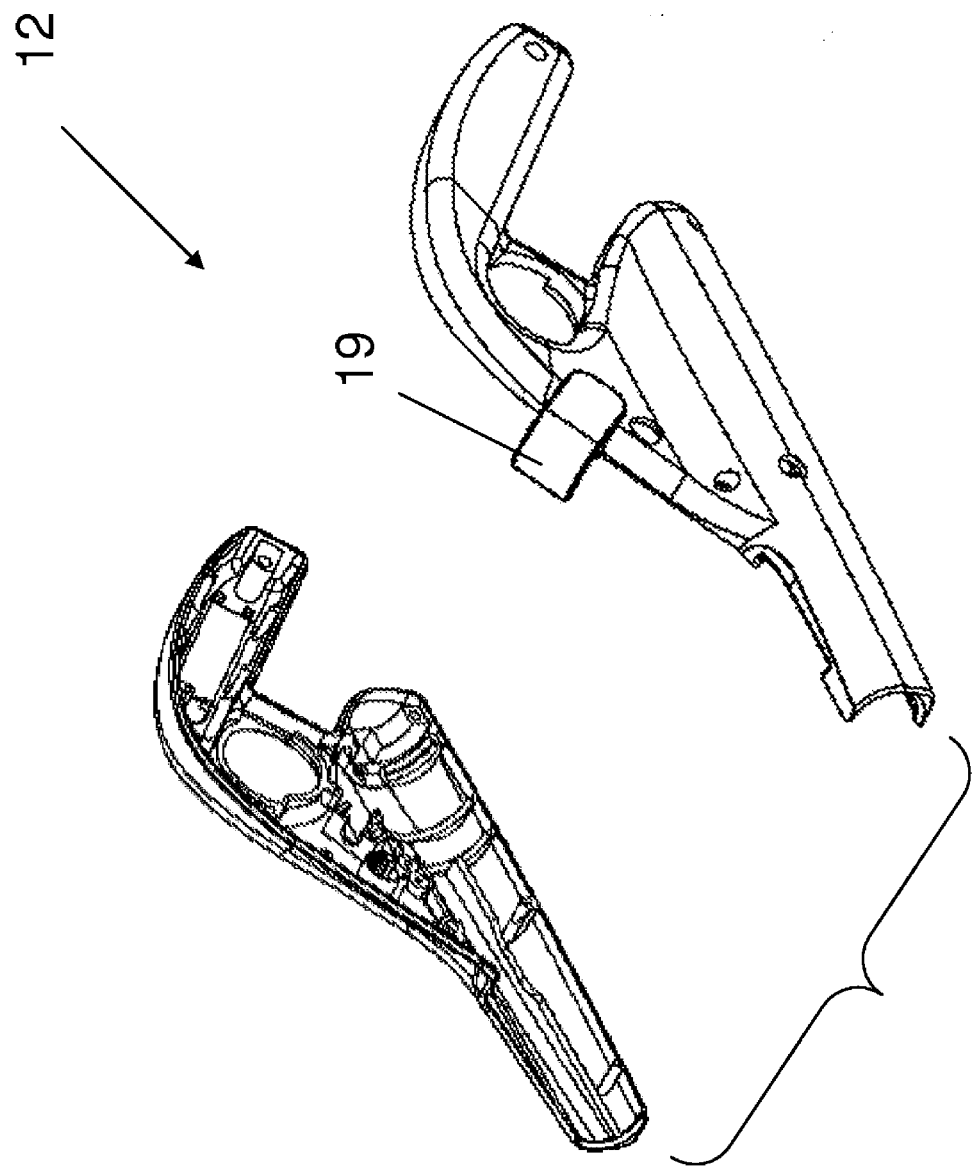
FIG. 7 illustrates an exemplary assembly of the handle of the embodiment depicted in FIG. 5.

FIG. 6 illustrates another embodiment of vascular treatment device 10. The handle may have a support 19 for the syringe 46 in the form of a hook, as described above. This embodiment may be assembled by mating two casings as shown in FIG. 7. The syringe may snap onto the support and remain in position during the use of the device. The support 19 (and/or handle 12) may be made of SLA resin or other materials that would allow the support to withstand the snapping force applied by the syringe.

Figure 8:
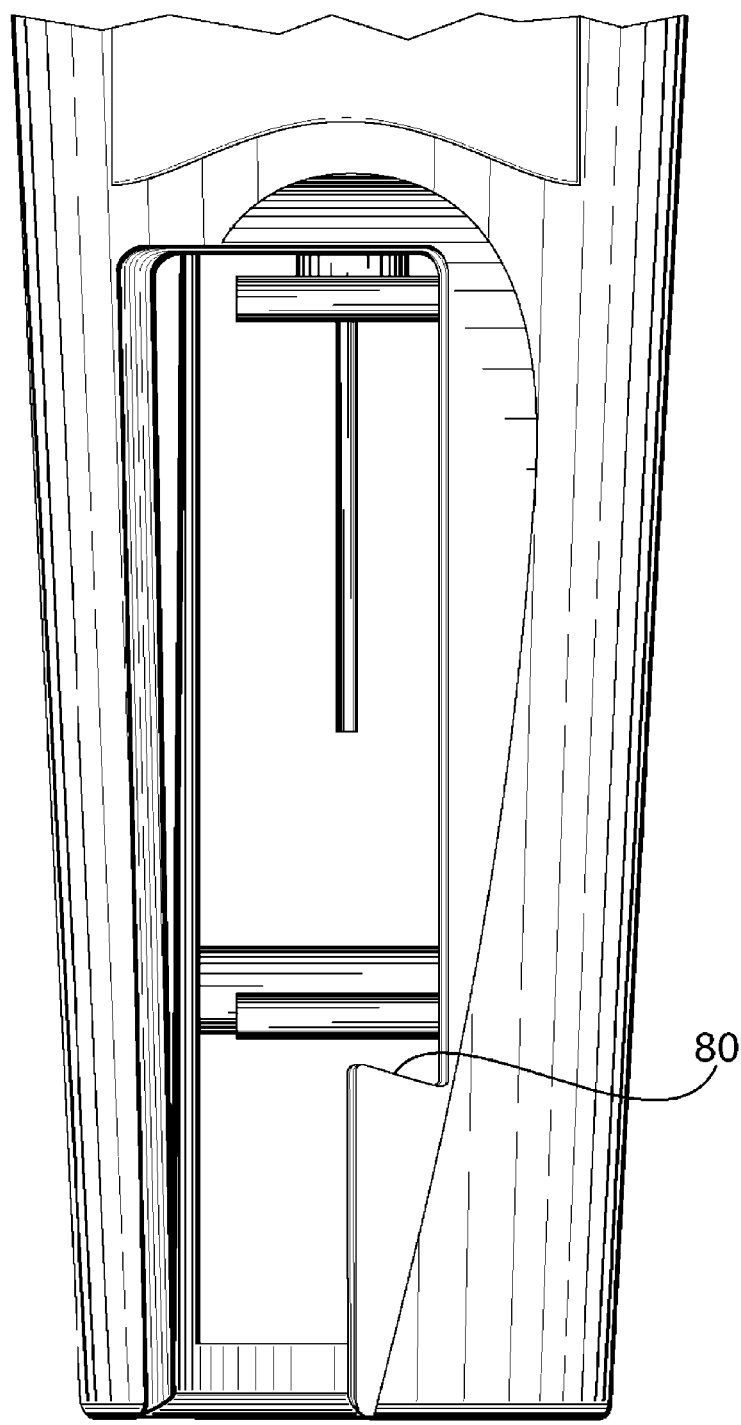
FIG. 8 depicts a top plan view of a portion of the handle illustrated in FIG. 7.

FIG. 8 shows a top view of the end of an alternate embodiment of handle 12 having a notch 80 for retaining the cartridge 14 (not shown) to the handle 12. In the previously mentioned embodiments, the handle had a switch that may be coupled to a gate which held the cartridge to the handle. In this configuration, the notch 80 may prevent the cartridge from disengaging from the handle. In use, a user may slide the cartridge into the handle and then "cock" the cartridge into notch 80 to prevent the cartridge from slipping out of the handle.

A wide variety of distal wire tips may be used; FIGS. 9-11, 14-14A, 15-15A, 16-16A, 17-17A, 18-18A, 19-19A, 20-20A, 21-21A, 22-22A, 23, and 24 show several examples.

Figure 9:
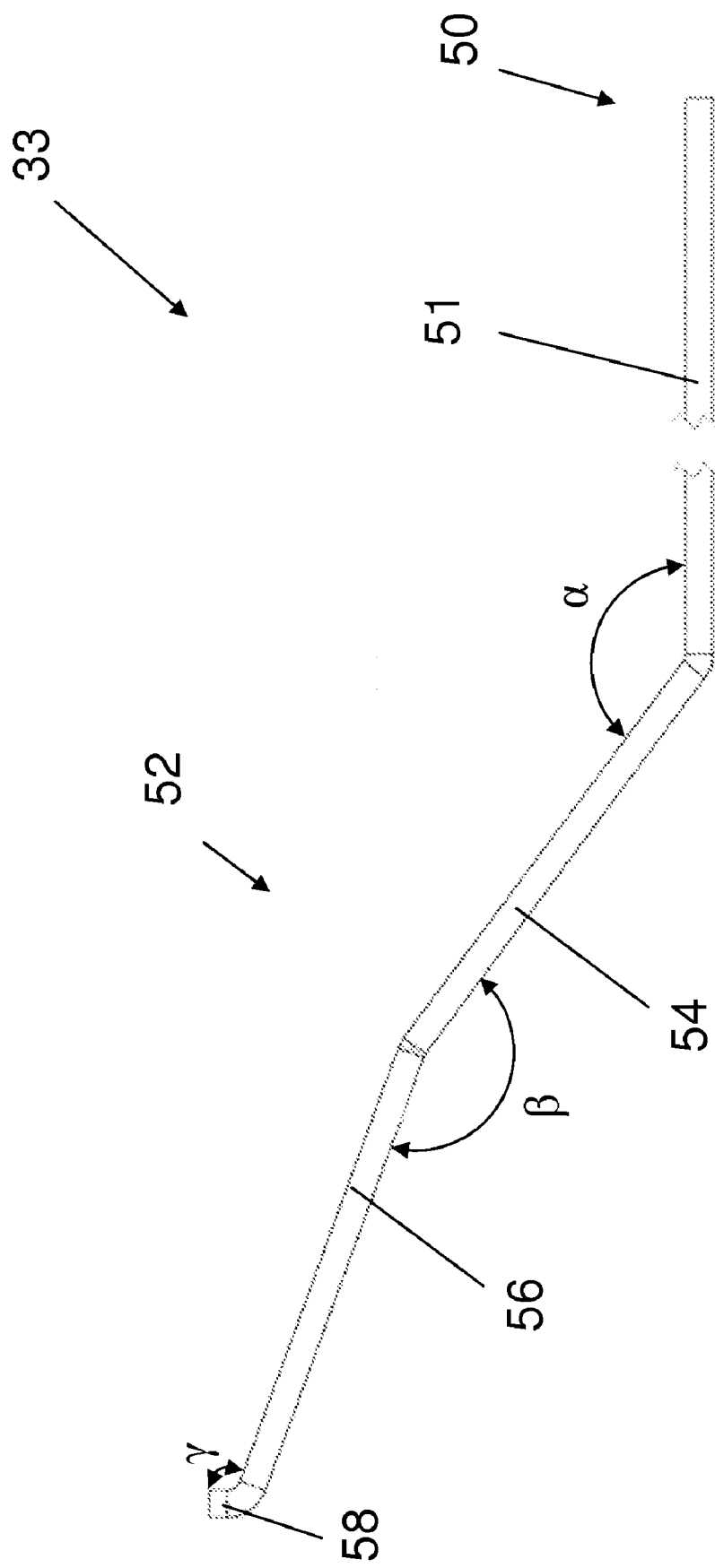
FIGS. 9-10 depict various embodiments of wire distal ends.

FIG. 9 shows an embodiment of a wire 33 having a proximal end 50, a distal end 52 and in proximal-to-distal order, a first segment 54, a second segment 56, and a third segment 58. The first segment 54 may extend between the main shaft 51 and the second segment 56 and may be biased to a first included angle $\alpha$ that is defined between the main shaft 51 and the first segment 54 and is less than 180 degrees. The second segment 56 may extend between the first segment 54 and the third segment 58 and may be biased to a second included angle $\beta$ that is defined between the first segment 54 and the second segment 56 and is less than 180 degrees. The third segment 58 may extend from the second segment 56 to a free end and may be biased to a third included angle $\gamma$ that is defined between the second segment 56 and the third segment 58 and is less than 180 degrees.

The second included angle may be greater than the first included angle. The sum of the first included angel and the third included angle, minus the second included angle, may be in the range of about 70 degrees to about 110 degrees. The sum of the first included angle and the third included angle, minus the second included angle may be in the range about 80 degrees to about 100 degrees. The sum of the first included angle and the third included angle, minus the second included angle may be about 90 degrees.

The third segment 58 of the wire 33 may have a length that is smaller than the inner diameter of the sheath 32. For example, the third segment 58 may have a length of less than 0.028 inches or it may have a length that is equal to or smaller than two-thirds of the inner diameter of the sheath 32.

The perpendicular distance measured from an center axis of the main shaft 51 to the free end may be less than 0.3 inches. The first segment 54 and the second segment 56 each may have a length in the range of about 0.2 inches to about 0.3 inches, or in the range about 0.24 inches to about 0.26 inches. The length of the first segment 54 may be in the range of about 0.248 inches to about 0.25 inches, and the length of the second segment is in the range of about 0.25 inches to about 0.252 inches. In one embodiment, the length of the first segment 54 may be 0.249 inches, and the length of the second segment is 0.2504 inches.

The distal end 52 of the wire 33 may include at least two linear segments oriented at a non-zero angle relative to one another. Having at least two linear segments may allow the distal tip of the wire to tuck into a sheath without touching the wall of the sheath, and it may also allow the main shaft of the wire to run along the vessel wall while the tip (for example, the third segment) of the wire digs into the vessel wall.

Figure 10:
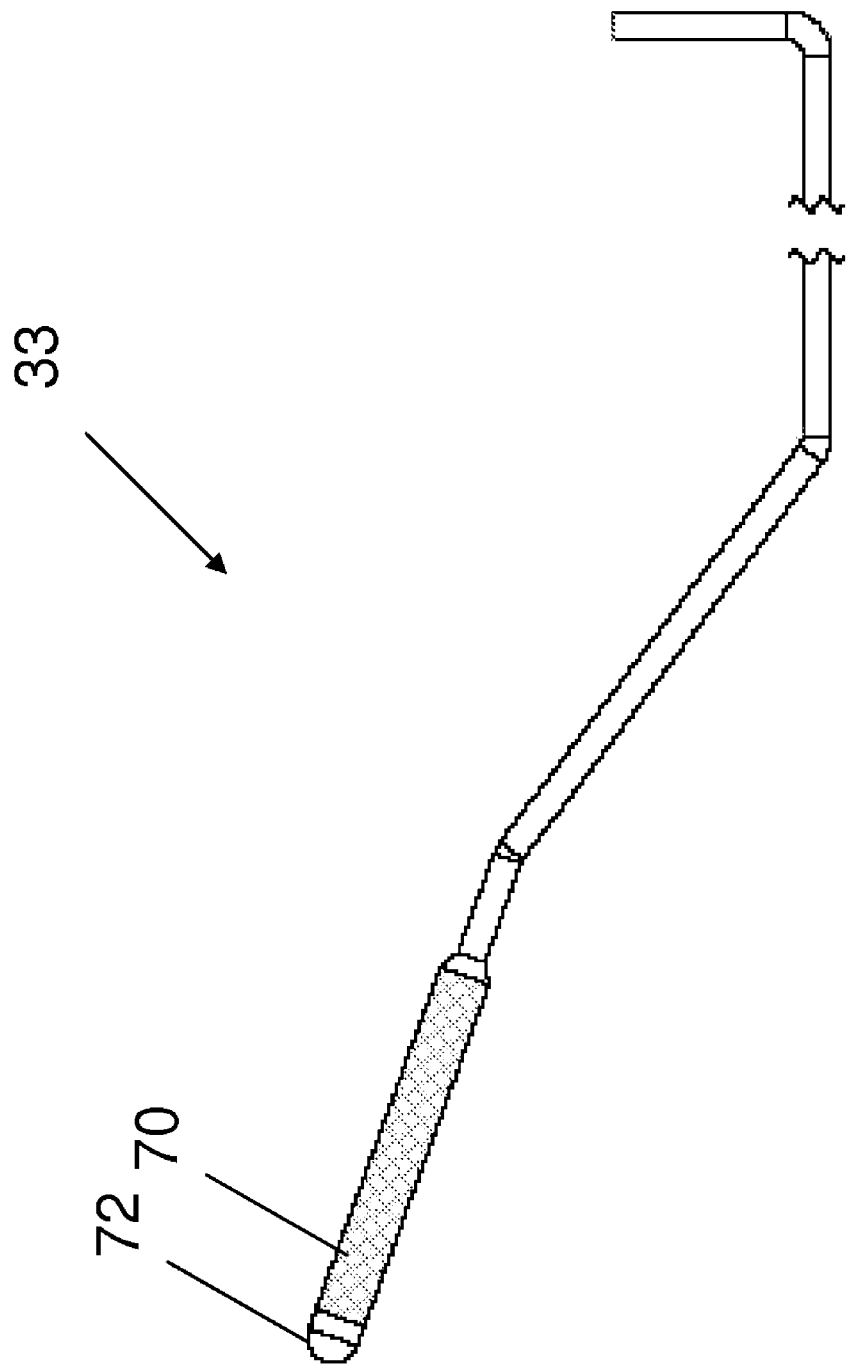

The wire tip located on the distal end 52 may have a wide variety of configurations, depending on the intended use. The wire shape may be "atraumatic," meaning that it may be shaped such that insertion causes little or no spasm or damage to the vessel. For example, FIG. 10 shows a distal end 52 terminating with a hemispheric free end. The hemispheric end may be textured or mechanically or chemically altered to create a roughened surface. Other atraumatic tips may include an end having a full radius, or a J-curved shape, or simply a curved shape.

FIG. 10 shows an atraumatic tip having a sleeve extending from the hemispheric shape along the wire 33 towards the proximal end of the wire. The sleeve 70 can add strength to the distal tip, thereby increasing the scrapping force and increasing the contact surface area to prevent detachment of the hemispheric tip 72.

In other embodiments, the distal tip 52 may be "aggressive" and be bent or curved so that it scrapes the vessel wall. FIG. 9 shows the distal end 52 having a flat free end with a sharp edge around. An aggressive distal tip 52 may also be created by beveling an edge to create a sharp point. The distal tip having a cutting blade, like a shark's fin, may also be aggressive. The distal tip 52 may be roughened to make the distal tip cut more aggressively and/or cause spasm to the blood vessel wall.

A roughened surface may be formed by subjecting an initially smooth steel to abrasion, machining, blasting, chemical etching such as acid etching (for example, nitric acid, hydrofluoric acid, hydrochloric acid, and/or sulfuric acid). A roughened outer surface may also be created by rolling a sheet metal, such as a sheet forming the sleeve 70, onto an irregularly shaped guide to create surface irregularity.

Also, the outer surfaces of the first, the second, and/or the third segments may be coated with an abrasive to roughen the surface. Other surface treatments may include a bastard cut file type or diamond grit. For example, 30 grit diamond may produce an aggressive surface and 200 grit diamond may produce a non-aggressive surface.

During use, especially with a roughened tip, the wire may be periodically re-encased in the sheath to help dislodge debris from the wire tip and keep the device operating normally.

An aggressive surface may also be formed on the first segment 54 and/or the second segments 56 of the wire 33 by introducing a screw threaded profile with a second wire along the length of the wire 33 by following a screw flights of various shapes such as a square, or a rhomboid, or a trapezoid, or a parallelogram, or an ellipse, or a triangle, or a pentagon.

FIG. 10 shows an embodiment having a first segment 56 with a sleeve 70 having a roughened outer surface using one of various methods mentioned earlier. In addition to showing a roughened surface treatment, FIG. 10 further illustrates a wire with a weight added at the distal tip, in this case the weight is added by a sleeve with a roughed outer surface. The weight may be centered on the wire or eccentrically positioned. An eccentric weight may cause the wire to flail about during rotation. The flailing may perturb the vessels more aggressively compared to a wire with centrically added weight.

The distal end 52 of the wire 33 may also include a curved segment. The curvature of the curved segment may be constant, or it may follow other curves, such as a sector of an ellipse or an oval. The distal end 52 of the wire 33 may also have a straight segment distal to the curved segment. Similar to the embodiments with a constant curvature, the curvature of the curved section with a straight segment may be constant or it may follow previously mentioned shapes.

Figure 13:
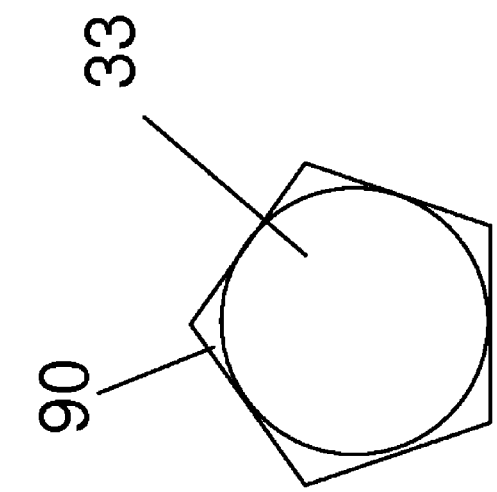
FIGS. 11-13 illustrate transverse cross-sectional views of various embodiments of wire distal tips about which springs are wrapped.
Figure 12:
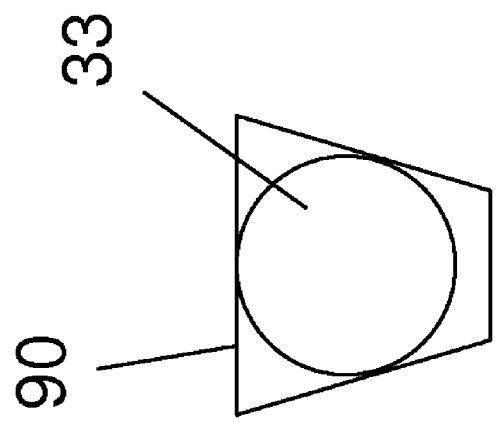
Figure 11:
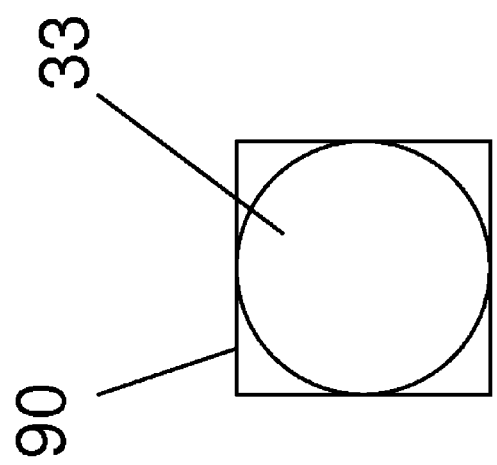

A spring 90 may be attached from the distal end 52 of the wire 33 along the first segment 54 and/or the second segment 56 to create an aggressive cutting surface. The ends of the spring may be brazed at multiple points. The spring 90 may follow the various profiles mentioned earlier. FIGS. 11-13 illustrate cross-sectional views of a spring following screw flights of a square, a trapezoid, and a pentagon, respectively.

The sharp corners of the various profiles (for example, a square, a triangle, a parallelogram, a pentagon) may dig into the blood vessel wall and ablate the vessel wall. The wire 33 may have a hemispheric or a flat free end depending on the intended use. The hemispheric end or flat free end may also be textured or roughened.

FIGS. 14-14A show a wire similar to that shown in FIG. 9 having first, second, and third linear segments distal to the main shaft.

Figure 15:
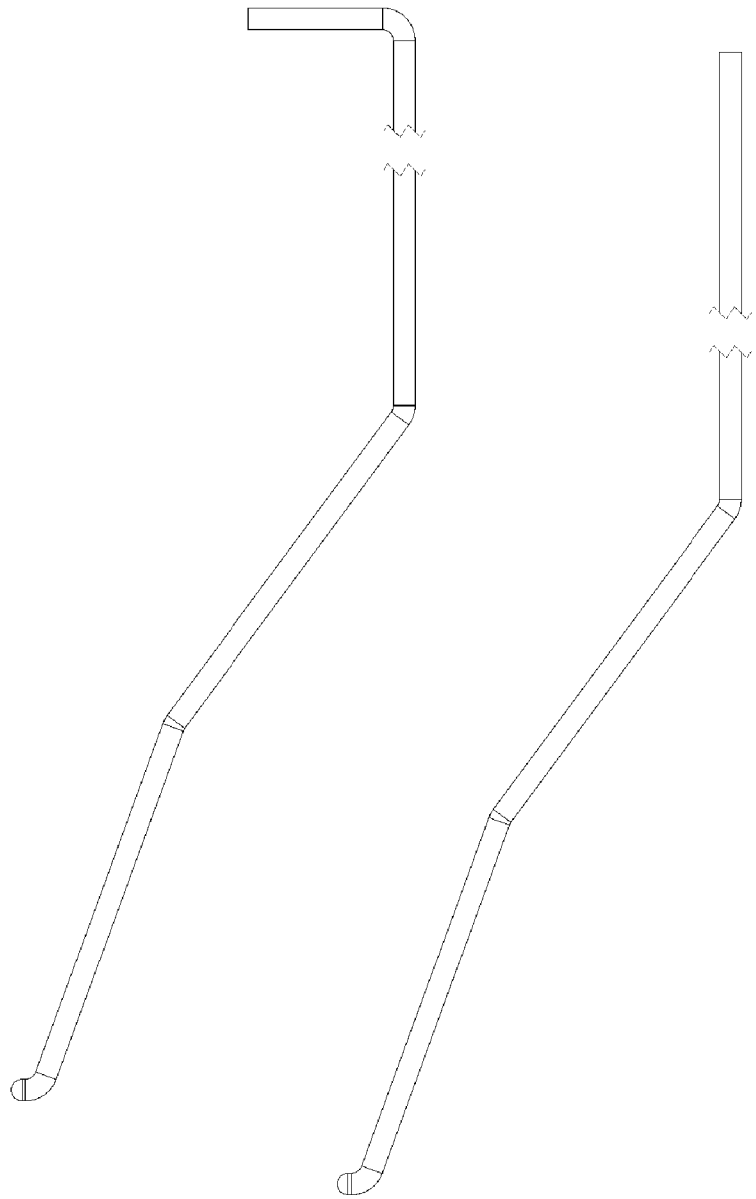

FIGS. 15-15A show a wire similar to that shown in FIGS. 14-14A, in which the free end of the third segment is hemispherical.

Figure 16:
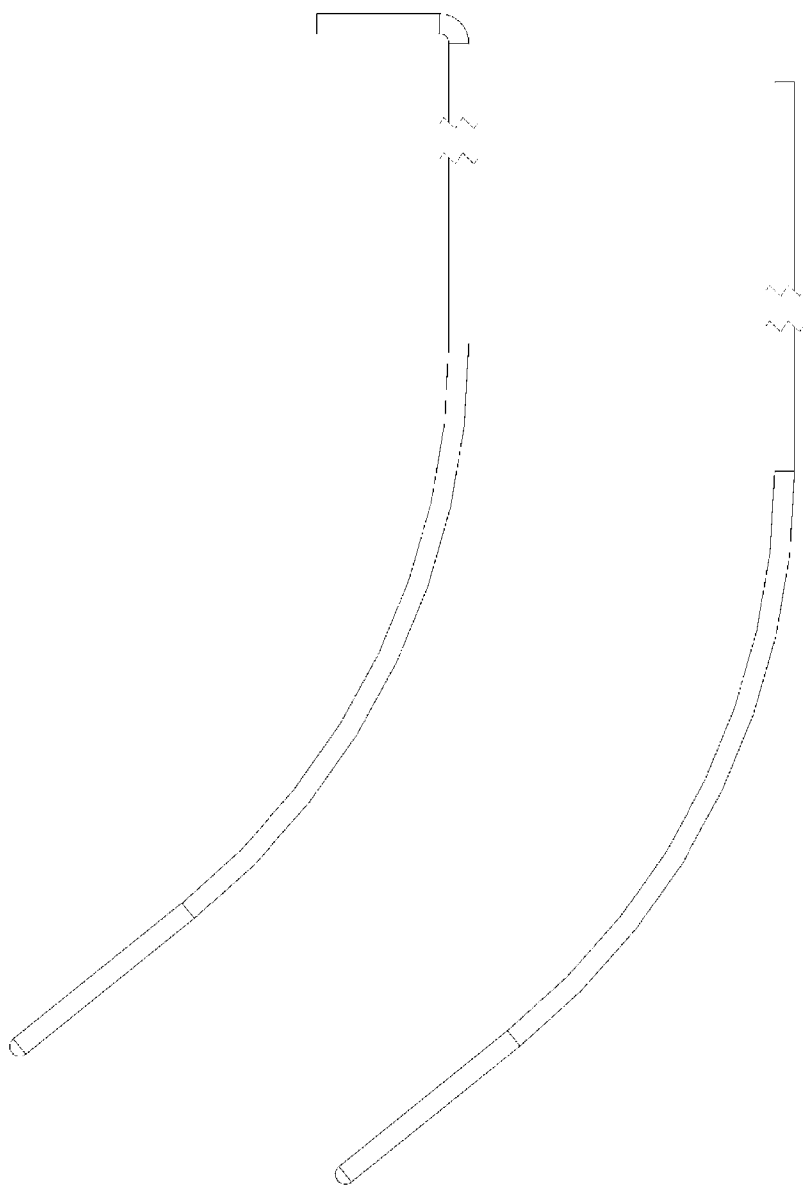

FIGS. 16-16A show a wire having a curved segment distal to the main shaft, and in which the free end of the curved segment is hemispherical.

Figure 17:
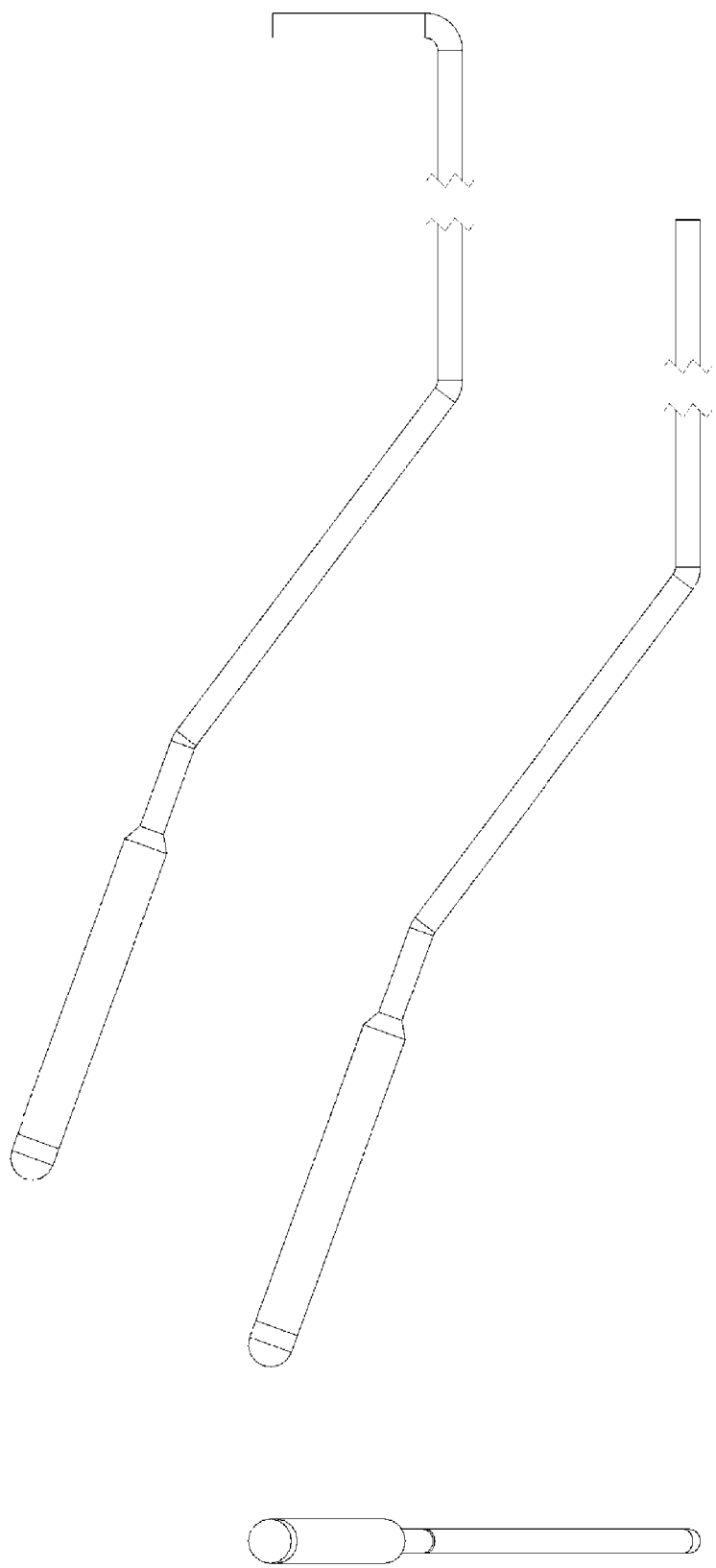

FIGS. 17-17A show a wire similar to that shown in FIG. 10 having first, second, and third linear segments, with weight added at the distal tip.

Figure 18:
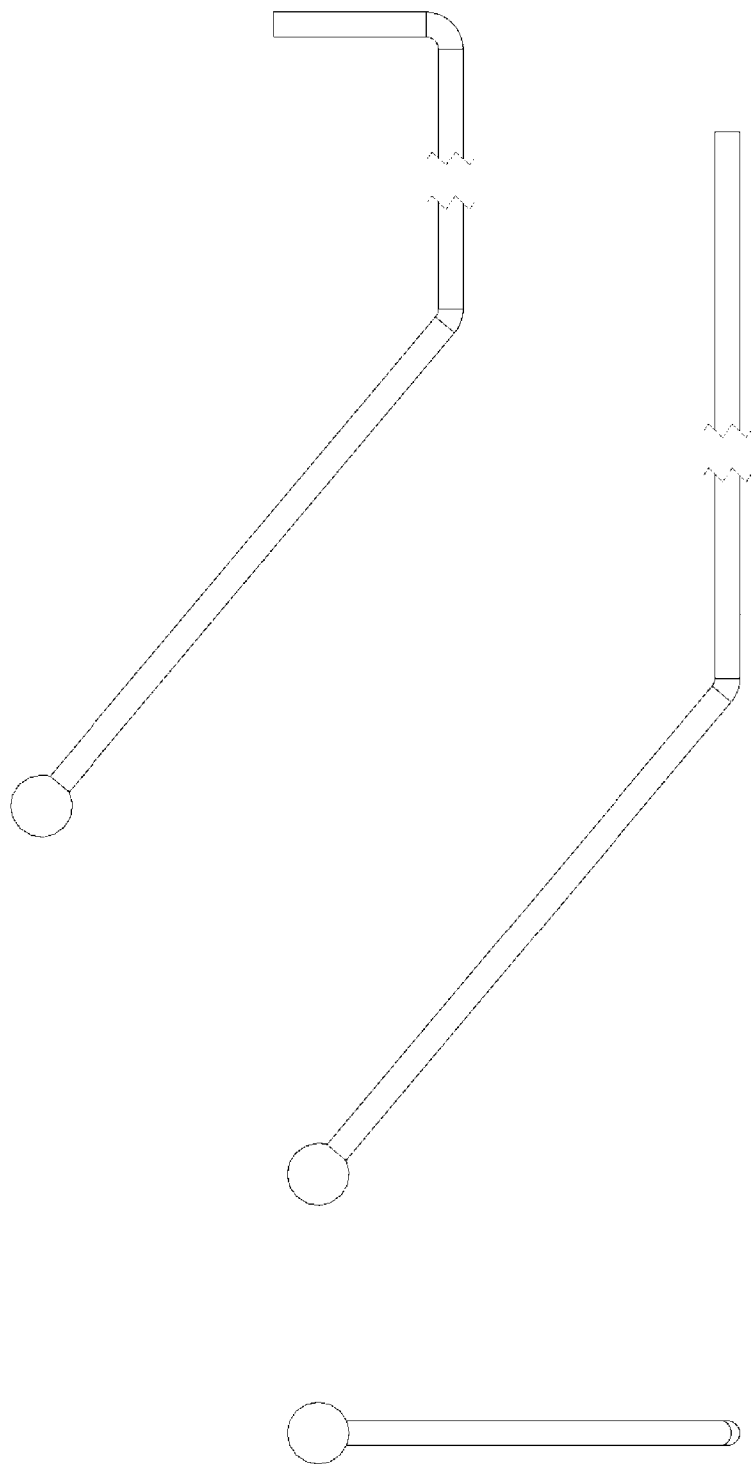

FIGS. 18-18A show a wire having a single linear segment distal to the main shaft, in which the linear segment terminates with a ball-shaped free end.

Figure 19:
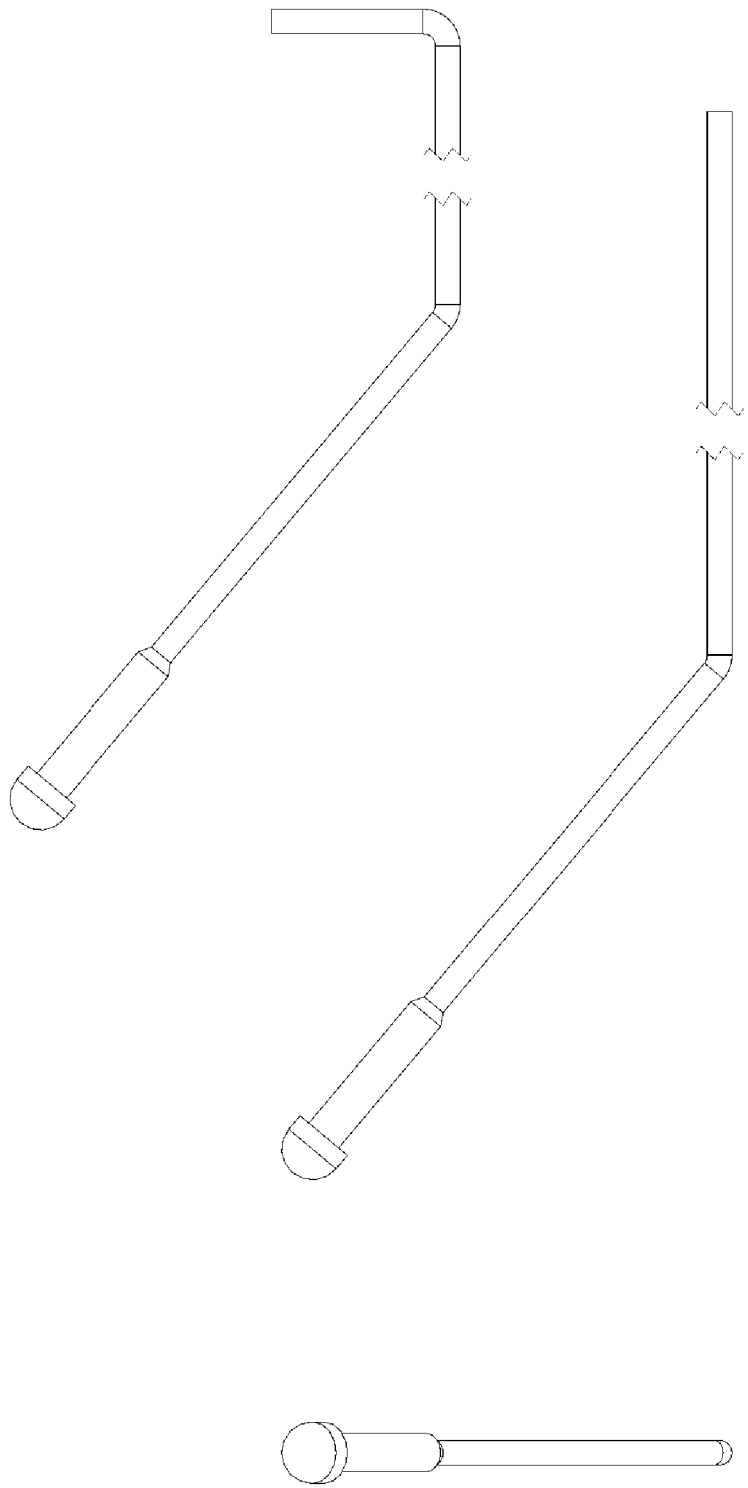

FIGS. 19-19A show a wire having a single linear segment distal to the main shaft, in which the distal tip has added weight and the free end is hemispherical.

Figure 20:
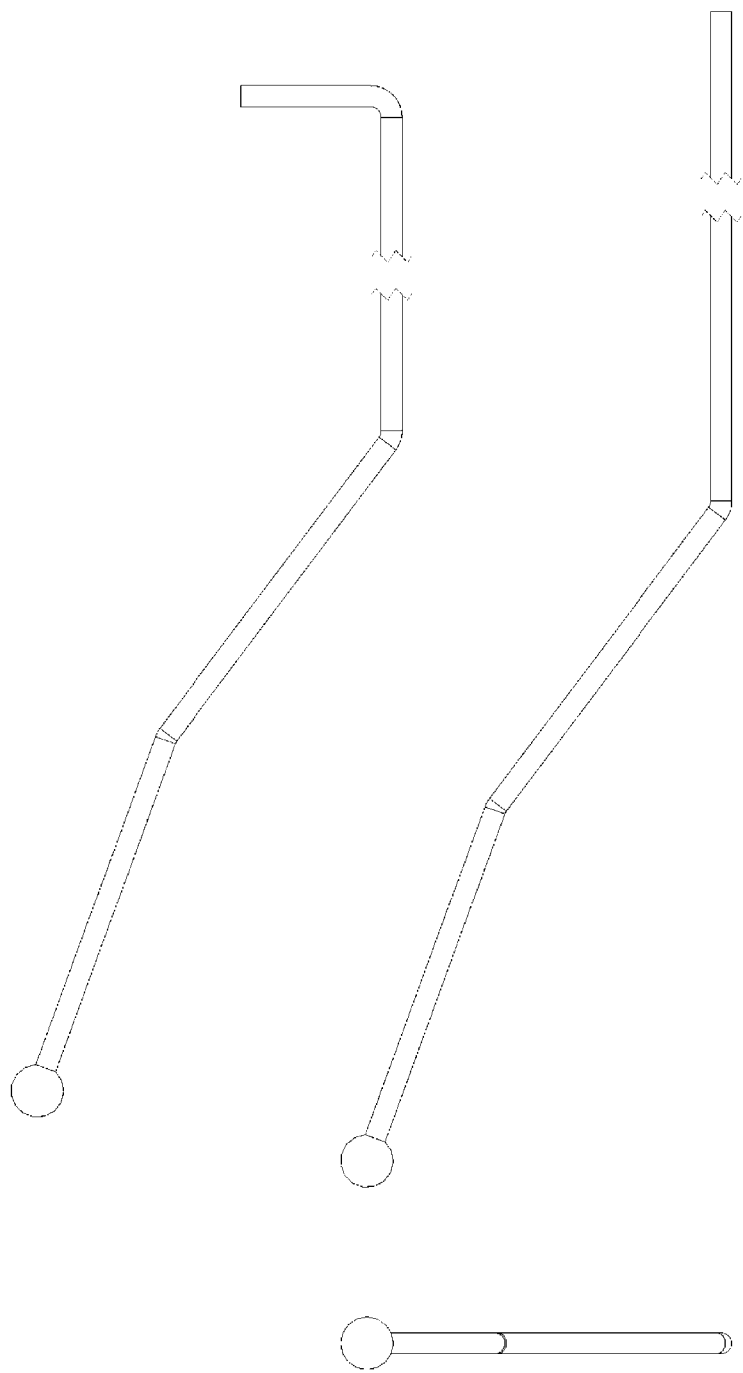

FIGS. 20-20A show a wire having two linear segments distal to the main shaft, in which the second linear segment terminates with a ball-shaped free end.

Figure 21:
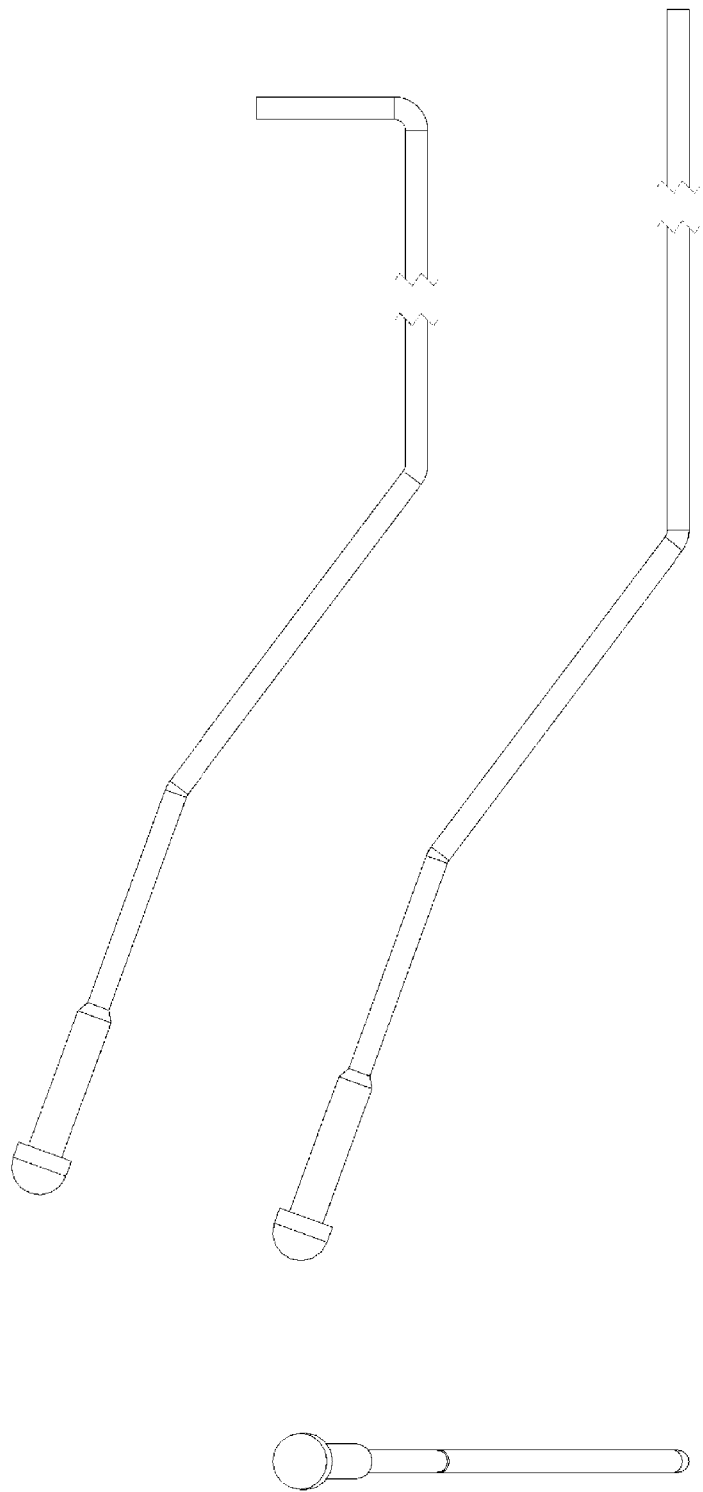

FIGS. 21-21A show a wire having two linear segments distal to the main shaft, in which the second linear segment has added weight and terminates with hemispherical free end.

Figure 22:
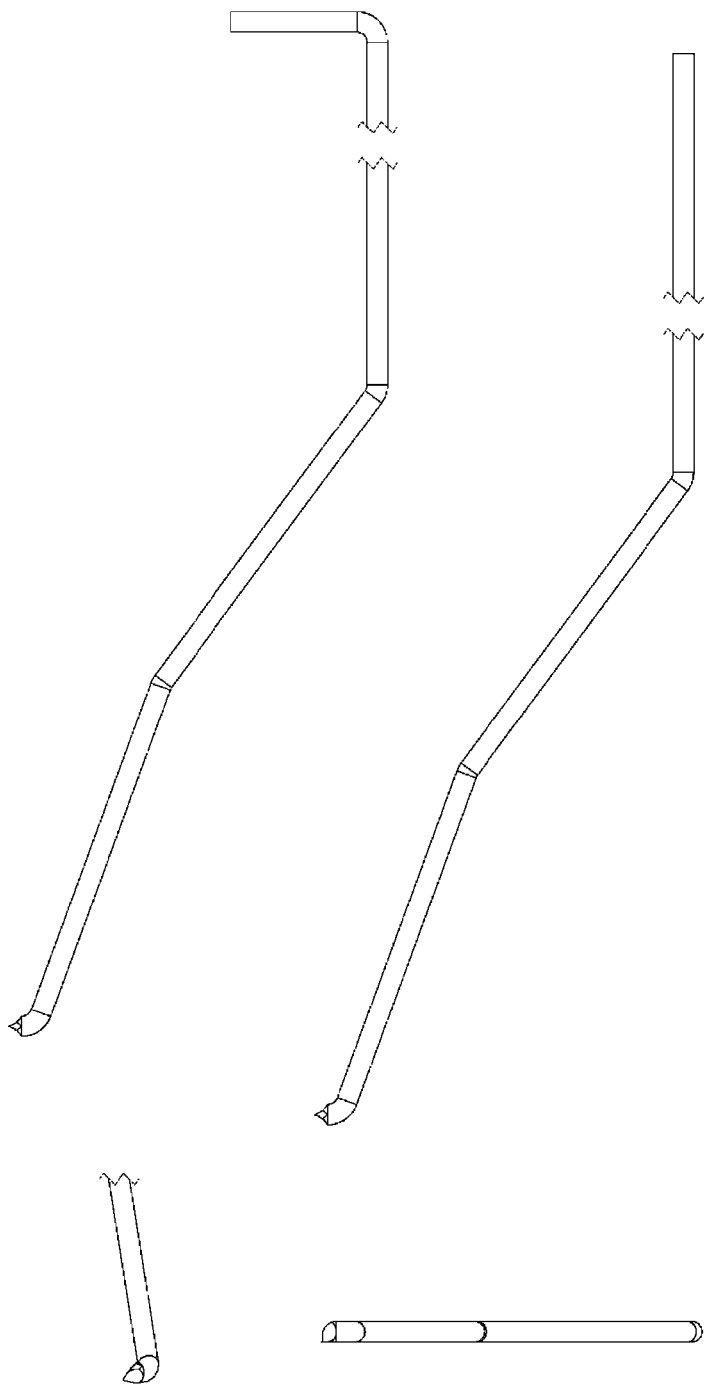

FIGS. 22-22A show a wire similar to that shown in FIGS. 14-14A, having three linear segments in which the third segment terminates with a sharp free end.

Figure 23:
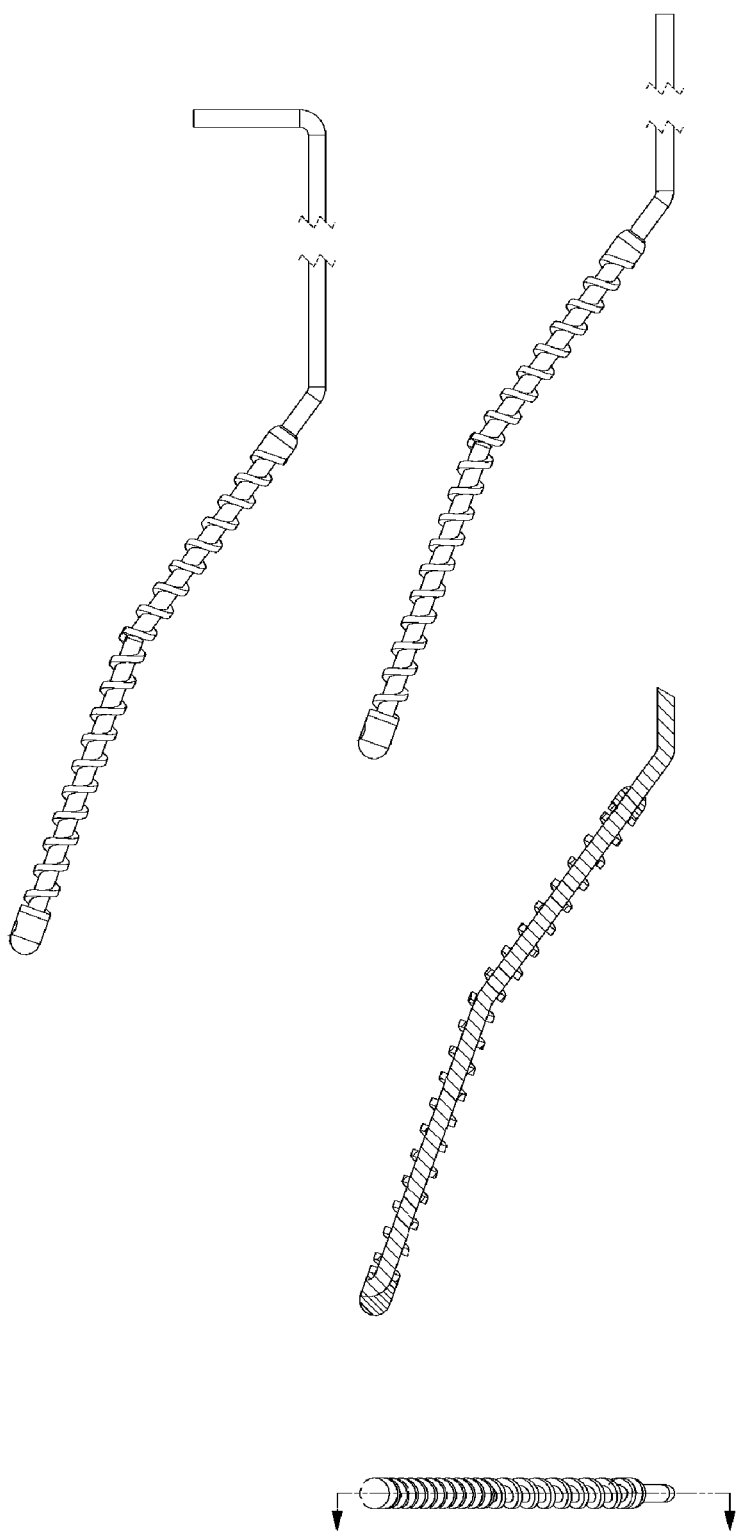
Figure 24:
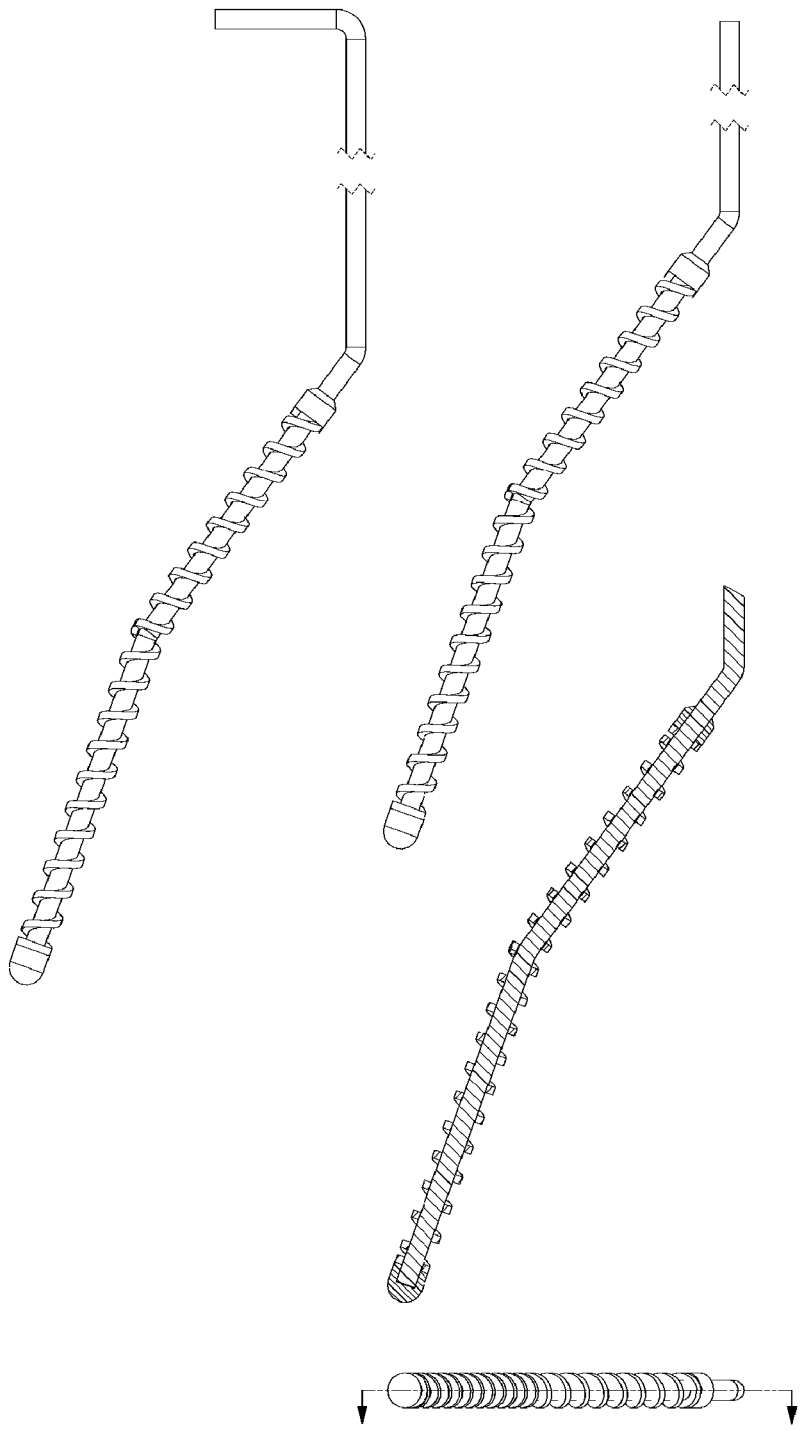

FIGS. 23-24 show wires having a spring wrapped around the distal portion of the wire.

We claim:

1. A vascular treatment device comprising:
   a handle having:
      a motor;
      a trigger mounted on the handle and transitionable between a first state that does not electrically couple the motor to a power source and a second state that does couple the motor to the power source; and
      a male coupling rotably driven by the motor; and
   a cartridge engageable with the handle and having:
      a female coupling so sized and shaped as to be engageable by, and once engaged by, to be rotated by the male coupling;
      a wire having a proximal end fixed to the female coupling, a main shaft extending therefrom and terminating at a distal end; and
      a sheath fixed to and extending from the cartridge, the sheath defining a lumen through which the wire runs;
   wherein the sheath, when the female coupling is not engaged by the male coupling, covers the distal end of the wire, and
   wherein as the male coupling and the female coupling fully engage each other and the cartridge is engaged with the handle, the male coupling displaces female coupling detents to allow the female coupling to slide within the cartridge, thereby causing the sheath, when the female coupling is engaged by the male coupling, to slide back relative to the wire and uncover the distal end of the wire.

2. The device of claim 1, further comprising a microswitch interposed in an electrical circuit connecting the trigger and the motor and transitionable by engagement of the cartridge and the handle from an open state to a closed state, thereby permitting the trigger and motor to be electrically coupled to one another.

3. The device of claim 1, wherein the system comprises a gate that is biased to a first position that prevents engagement of the cartridge and the handle and is transitionable to a second position that permits engagement of the cartridge and the handle.

4. The device of claim 3, wherein the gate is further transitionable to a third position that prevents disengagement of the cartridge and the handle.

5. The device of claim 4, wherein the third position is intermediate the first and second positions.

6. The device of claim 4, wherein the gate, when in the third position, is received in a detent defined in the cartridge.

7. The device of claim 3, wherein the gate is biased to the first position by a spring contacting the handle.

8. The device of claim 3, wherein the gate is physically coupled to a switch on the handle such that movement of the switch transitions the gate between the first position and the second position.

9. The device of claim 1, wherein the handle includes a potentiometer electrically coupled to the motor to control a speed of the motor.

10. The device of claim 1, wherein the male coupling is biased toward an expanded state and transitionable from the expanded state to a contracted state.

11. The device of claim 10, wherein the female coupling is so sized and shaped as to transition the male coupling from the expanded state to the contracted state during engagement of the handle and the cartridge.

12. The device of claim 10, wherein the male coupling is so sized and shaped as to return to the expanded state once the cartridge and the handle are fully engaged.

13. The device of claim 10, wherein the male coupling comprises at least two prongs separated by slitted portions.

14. The device of claim 1, wherein the sheath has an inner diameter between 0.022 inches to 0.048 inches.

15. The device of claim 1, wherein the sheath has an outer diameter between 0.020 inches to 0.050 inches to facilitate insertion into a vein.

16. The device of claim 1, wherein one or more portions of the handle define a trigger ring in which the trigger is at least partly disposed, and wherein the handle is so arranged as to be balanced when supported from only one or more portions of the handle that define the trigger ring.

17. The device of claim 1, wherein the sheath comprises external markings at regular intervals.

18. The device of claim 1, wherein:
the distal end comprises, in proximal-to-distal order, a first segment, a second segment, and a third segment;
the first segment extends between the main shaft and the second segment and is biased to rest at a first included angle that is:
defined between the main shaft and the first segment; and
less than 180 degrees;
the second segment extends between the first segment and the third segment and is biased to rest at a second included angle that is:
defined between the first segment and the second segment; and
is less than 180 degrees; and
the third segment extends from the second segment to a free end and is biased to rest at a third included angle that is:
defined between the second segment and the third segment; and
is less than 180 degrees.

19. The device of claim 18, wherein the second included angle is greater than the first included angle.

20. The device of claim 18, wherein the sum of the first included angle and the third included angle, minus the second included angle, is in the range of about 70 degrees to about 110 degrees.

21. The device of claim 20, wherein the sum of the first included angle and the third included angle, minus the second included angle, is in the range of about 80 degrees to about 100 degrees.

22. The device of claim 21, wherein the sum of the first included angle and the third included angle, minus the second included angle, is about 90 degrees.

23. The device of claim 18, wherein the third segment has a length that is smaller than an inner diameter of the sheath.

24. The device of claim 23, wherein the third segment has a length of less than 0.028 inches.

25. The device of claim 23, wherein the third segment has a length that is equal to or smaller than two-thirds of the inner diameter of the sheath.

26. The device of claim 18, wherein a perpendicular length measured from an axis defined by the main shaft to the free end is less than 0.3 inches.

27. The device of claim 18, wherein the first and second segments each have a length in the range of about 0.2 inches to about 0.3 inches.

28. The device of claim 27, wherein the first and second segments each have lengths in the range of about 0.24 inches to about 0.26 inches.

29. The device of claim 28, wherein the length of the first segment is in the range of about 0.248 inches to about 0.25 inches, and the length of the second segment is in the range of about 0.25 inches to about 0.252 inches.

30. The device of claim 29, wherein the length of the first segment is 0.249 inches, and the length of the second segment is 0.2504 inches.

31. The device of claim 18, wherein the distal end has at least two linear segments oriented at a non-zero angle relative to one another.

32. The device of claim 18, wherein the free end is ball-shaped.

33. The device of claim 1, wherein the distal end of the wire terminates with a hemispheric free end.

34. The device of claim 1, wherein the distal end of the wire terminates with a pointed free end.

35. The device of claim 1, wherein the distal end of the wire terminates with a textured hemispheric free end.

36. The device of claim 1, wherein the distal end of the wire terminates with a flat free end.

37. The device of claim 1, wherein the wire distal end is weighted.

38. The device of claim 37, wherein the distal end is eccentrically weighted relative to the main shaft.

39. The device of claim 1, wherein the distal end has a roughened surface.

40. The device of claim 1, wherein the wire further comprises a spring attached along the distal end.

41. The device of claim 1, wherein the wire distal end comprises a curved segment.

42. The device of claim 41, wherein the wire distal end comprises a straight segment distal to the curved segment.

43. The device of claim 1, further comprising a syringe in fluid communication with the sheath lumen.

44. The device of claim 43, wherein the syringe is attached to the cartridge.

45. The device of claim 43, wherein the syringe is attachable to the cartridge with or without a stopcock.

46. The device of claim 43, wherein the handle further comprises a support so positioned as to receive the syringe.

47. The device of claim 43, wherein the handle and the syringe are so sized, shaped, and positioned as to permit a user to actuate the trigger with the index finger of a hand and simultaneously depress a plunger into the syringe with the thumb of the same hand.

48. The device of claim 1, wherein the handle:
comprises a casing formed from two pieces;
contains the motor and the male coupling; and
defines a receptacle in which the male coupling is positioned and which receives the female coupling of the cartridge when the cartridge and the handle engage.

49. The device of claim 1, wherein the distal end of the wire comprises a single linear segment extending between the main shaft and a ball-shaped free end and is biased to rest at a first included angle that is defined between the main shaft and the linear segment and is less than 180 degrees.

50. The device of claim 49, wherein the first included angle is 140 degrees.

\* \* \* \* \*